United States Patent
Kiser et al.

(10) Patent No.: US 9,226,894 B2
(45) Date of Patent: *Jan. 5, 2016

(54) INTRAVAGINAL DEVICES FOR CONTROLLED DELIVERY OF LUBRICANTS

(71) Applicant: The University of Utah Research Foundation, Salt Lake City, UT (US)

(72) Inventors: Patrick F. Kiser, Chicago, IL (US); R. Tyler McCabe, North Salt Lake City, UT (US); Margaret N. Kiser, Chicago, IL (US); Theodore Henry Albright, Reno, NV (US)

(73) Assignee: THE UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,138

(22) Filed: May 11, 2015

(65) Prior Publication Data

US 2015/0238415 A1 Aug. 27, 2015

Related U.S. Application Data

(63) Continuation of application No. 13/884,936, filed as application No. PCT/US2011/060389 on Nov. 11, 2011, now Pat. No. 9,078,813.

(60) Provisional application No. 61/413,238, filed on Nov. 12, 2010, provisional application No. 61/516,582, filed on Apr. 5, 2011, provisional application No. 61/542,552, filed on Oct. 3, 2011.

(51) Int. Cl.
*A61K 9/00* (2006.01)
*A61M 31/00* (2006.01)

(52) U.S. Cl.
CPC ............. *A61K 9/0036* (2013.01); *A61K 9/0092* (2013.01); *A61M 31/002* (2013.01)

(58) Field of Classification Search
None
See application file for complete search history.

(56) References Cited

U.S. PATENT DOCUMENTS 4,331,786 A   5/1982   Foy et al.
4,332,920 A   6/1982   Foy et al.

(Continued)

OTHER PUBLICATIONS

Gnanou, Y., et al., "Hydrophilic polyurethane networks based on poly(ethylene oxide): synthesis, characterization, and properties," 1984, Macromolecules, 17(4), pp. 945-952.

(Continued)

*Primary Examiner* — Robert A Wax
*Assistant Examiner* — Melissa Mercier
(74) *Attorney, Agent, or Firm* — Foley & Lardner LLP

(57) ABSTRACT

The present technology provides intravaginal devices designed to deliver lubricants to the vagina for a sustained period of time. The intravaginal devices include a first segment comprising an outer surface and a lumen containing a lubricant, wherein the first segment is configured to deliver the contents of the lumen to the outer surface, and the first segment comprises a polymer selected from the group consisting of a hydrophilic, semi-permeable elastomer and a hydrophobic elastomer. The lubricant may be an aqueous lubricant. The present technology further provides an intravaginal device including a solid first segment that includes a hydrophilic semi-permeable elastomer, an outer surface and an aqueous lubricant, wherein the first segment is configured to deliver the aqueous lubricant to the outer surface.

29 Claims, 4 Drawing Sheets

(56) References Cited

U.S. PATENT DOCUMENTS

| | | | |
|---|---|---|---|
| 4,361,680 | A | 11/1982 | Borg et al. |
| 4,663,148 | A * | 5/1987 | Eckenhoff et al. ............ 424/454 |
| 4,743,673 | A | 5/1988 | Johnston et al. |
| 5,120,816 | A | 6/1992 | Gould et al. |
| 5,589,563 | A | 12/1996 | Ward et al. |
| 5,756,632 | A | 5/1998 | Ward et al. |
| 5,972,372 | A | 10/1999 | Saleh et al. |
| 6,197,327 | B1 | 3/2001 | Harrison et al. |
| 2006/0185678 | A1 | 8/2006 | Bronnenkant et al. |
| 2007/0043332 | A1 * | 2/2007 | Malcolm et al. ............ 604/500 |
| 2007/0254014 | A1 | 11/2007 | Ahmed et al. |
| 2008/0069850 | A1 | 3/2008 | Shalaby et al. |
| 2008/0140185 | A1 | 6/2008 | Kiser et al. |
| 2009/0004246 | A1 | 1/2009 | Woolfson et al. |
| 2010/0285097 | A1 | 11/2010 | Talling et al. |
| 2010/0316691 | A2 | 12/2010 | Kiser et al. |
| 2011/0045076 | A1 | 2/2011 | Kiser et al. |
| 2014/0209100 | A1 | 7/2014 | Kiser et al. |

OTHER PUBLICATIONS

International Preliminary Report on Patentability and Written Opinion received for PCT/US2011/060389 mailed May 23, 2013.
International Search Report and Written Opinion received for PCT/US2011/060389 mailed May 29, 2012.
McMillin, C.R., "Biomedical Applications of Rubbers and Elastomers," Rubber Chemistry and Technology: Jul. 2006, vol. 79, No. 3, pp. 500-519.
Pujol, J.M., "Progress in Organosilicon Chemistry," Jubilee International Symposium on Organosilicon Chemistry, 10th, Poznan, Aug. 1993 (1995), pp. 503-521.
Syzcher, M., "Szycher's Handbook of Polyurethanes," 1999, CRC Press, Chapter 3: Structure-Property Relations in Polyurethanes, pp. 3-1 to 3-40 and 11-1 to 11-23.
US Notice of Allowance DTD Dec. 19, 2014.
US Notice of Allowance DTD Feb. 27, 2015.
Zdrahala, R.J., et al., "Utilization of polyurethanes in biomedical applications: past promises, present realities and a vibrant future," J. Biomater. Appl., 14, pp. 67-90.

* cited by examiner

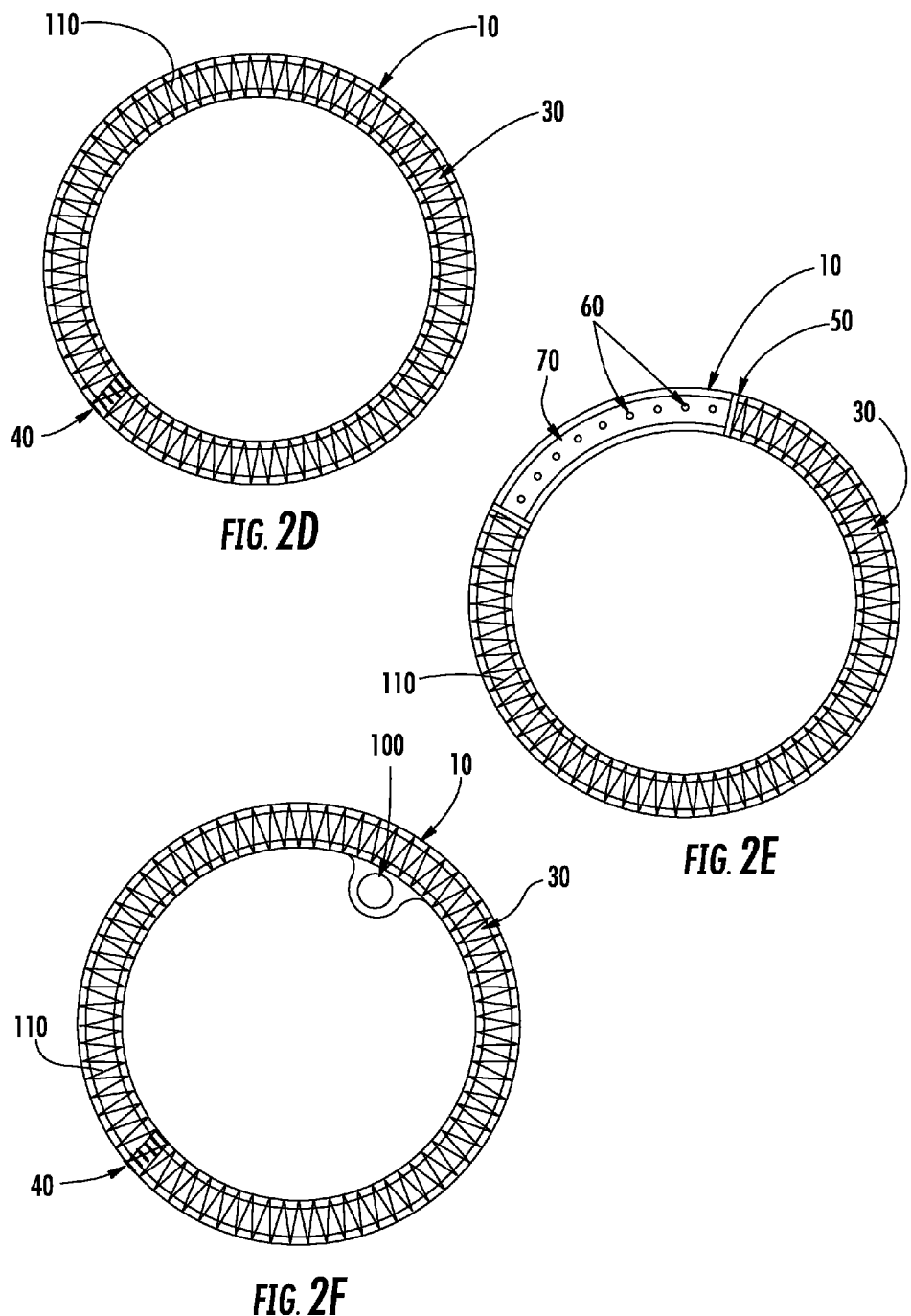

INTRAVAGINAL DEVICES FOR CONTROLLED DELIVERY OF LUBRICANTS

CROSS-REFERENCE TO RELATED APPLICATIONS

This application is a continuation of U.S. application Ser. No. 13/884,936 filed Nov. 12, 2013, which is a U.S. national phase application of International Application Serial No. PCT/US2011/060389, filed on Nov. 11, 2011, which claims priority to U.S. Provisional Application No. 61/413,238 filed Nov. 12, 2010, U.S. Provisional Application No. 61/516,582 filed Apr. 5, 2011, and U.S. Provisional Application No. 61/542,552 filed Oct. 3, 2011, the contents of each of which are incorporated herein by reference in their entirety.

FIELD OF TECHNOLOGY

The present technology relates to devices and methods for intravaginal delivery of lubricants, including, e.g., aqueous and non-aqueous, including hypo-osmotic, iso-osmotic, and hyper-osmotic lubricants, water and gels.

BACKGROUND

Vaginal dryness is a common problem for many women. Although it is traditionally considered to be a condition that affects postmenopausal women, it can occur during the pre-menopausal and perimenopausal years, as well as throughout their lifetime. Current therapies for increasing vaginal moisture include lubricating creams or jellies, topical estrogen creams, and HRT (hormone replacement therapy). Lubricating jellies are often messy to use and provide short-lived and temporary relief. Topical estrogen creams, if used on a regular basis, may be absorbed into the systemic circulation. This can cause endometrial stimulation and can lead to endometrial hyperplasia and carcinoma. HRT is widely used and effective at relieving symptoms of, e.g., vaginal atrophy and hence vaginal dryness. However, recent studies indicate that HRT can increase risk of heart attacks, stroke, blood clots, and breast cancer in some women.

BRIEF DESCRIPTION OF THE DRAWINGS

FIG. 2 A-F shows six illustrative embodiments of IVRs of the present technology. FIGS. 2D, 2E, and 2F illustrate supported variations of the various IVRs. In each of the IVRs of FIGS. 2D, 2E, and 2F, support springs are incorporated into the walls of, respectively, the single segment IVR of FIG. 2A, the dual segment IVR of FIG. 2B and the pod-containing IVR of FIG. 2C.

DETAILED DESCRIPTION

Figure 1:
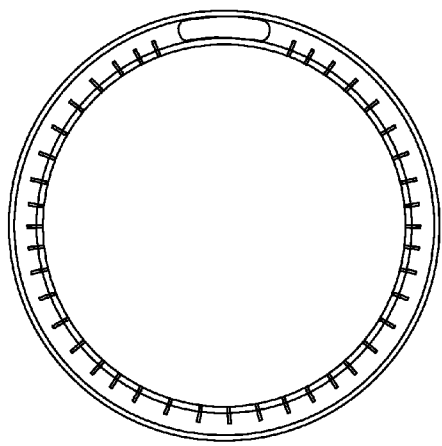
FIG. 1 shows an illustrative embodiment of an intravaginal device (IVD) of the present technology that is an intravaginal ring (IVR) having a single segment and including multiple slits. The IVR is constructed of hydrophobic elastomeric tubing, which contains a vaginal lubricant in the lumen. The ends of the tubing are joined by a plug, which fits within each end of the tubing.
Figure 2A:
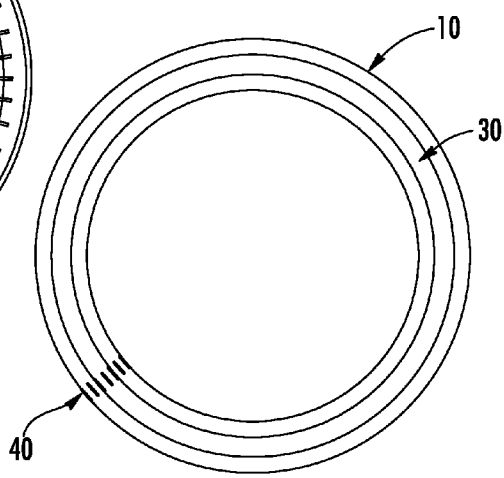
FIG. 2A shows an IVR constructed from a semi-permeable elastomer 10 to allow for the diffusion of lubricant from the lumen 30, through the hydrophilic elastomer, to the outer surface of the ring. The IVR is formed from a single segment of hydrophilic elastomeric tubing joined by a plastic weld 40.
Figure 2B:
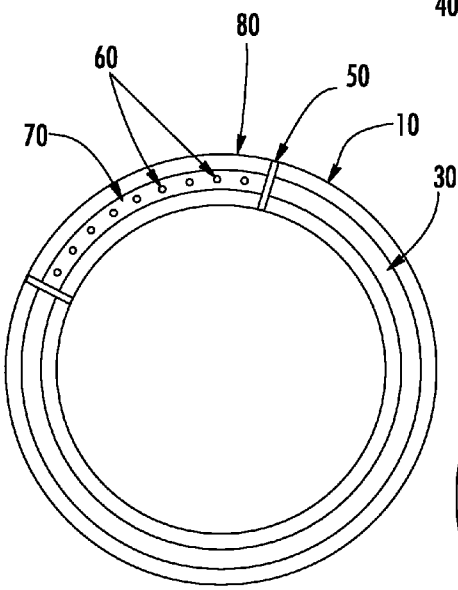
FIG. 2B shows a dual segment IVR. One segment of this IVR is constructed from a semi-permeable elastomer 10 having a lumen 30 filled with lubricant. A second segment 80 is constructed out of a hydrophobic elastomer with pores or holes 60 that extend from the surface of the segment to the lumen 70, which is filled with a lubricant as well (e.g., a gel). The two segments are joined at the ends and the lumens are separated by polymer plugs 50.
Figure 2C:
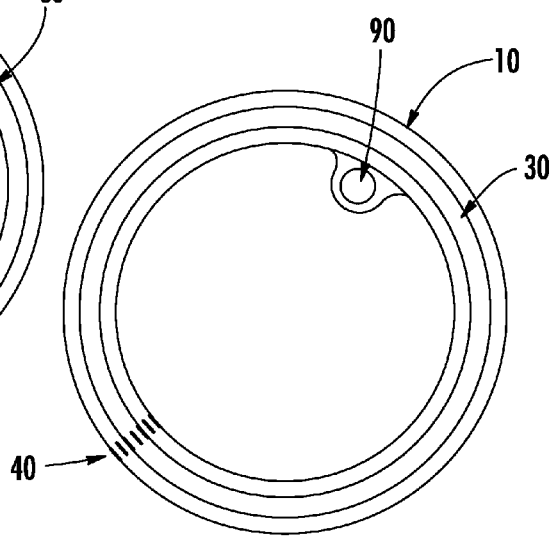
FIG. 2C shows an IVR similar to the one shown in FIG. 2A, but including a pod that may contain additional lubricant (the same or different from that in lumen 30) or other additives for regulating the vaginal environment, e.g., probiotics.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here.

The present technology provides devices and methods for intravaginal delivery of lubricants such as aqueous lubricants. Lubricants of the present technology include only those lubricants that are suitable for use on vaginal tissues. By "aqueous lubricant" is meant water or any water-based solution, emulsion, suspension, gel or foam that can provide lubrication and moisture to the vaginal tissues. In particular, use of intravaginal devices of the present technology directly relieve the symptoms of vaginal atrophy, dryness, irritation, pain and discomfort. The aqueous lubricants released by the present devices can soothe and revitalize or restore dry tissues within the vaginal mucosa. The lubricants may also be formulated to maintain appropriate pH and physiology and promote a normal vaginal environment. Thus, the present devices are non-irritating, safe, easy to use, and typically, hormone free. They may be designed for use over several hours, a single day or continuously for up to 30 days.

In accordance with one aspect, the present technology provides intravaginal devices that include a first segment that includes an outer surface and a lumen containing a lubricant, e.g., an aqueous lubricant, moisturizing or wetting agent. The first segment is configured to deliver the contents of the lumen to the outer surface, for example, in a controlled or sustained fashion. The first segment includes a polymer selected from the group consisting of a hydrophilic, semi-permeable elastomer and a hydrophobic elastomer. Alternatively, the intravaginal device may include a solid first segment, which includes a hydrophilic semi-permeable elastomer, an outer surface, and an aqueous lubricant, wherein the first segment is configured to deliver the aqueous lubricant to the outer surface. The devices may be an intravaginal ring, a tampon-shaped device, or any other size and shape suitable for residence in a subject's vagina. Thus, when the device is placed in the subject's vagina, lubricant delivered to the outer surface of the device will be available for lubrication of vaginal tissues. The elastomer is not gelatin and does not dissolve in the vaginal environment.

As noted above, the first segment of the intravaginal device may include a hydrophilic, semi-permeable elastomer. Because such polymers are semi-permeable, they allow the aqueous lubricant to slowly diffuse from the lumen to the outer surface of the device. No macroscopic channels such as slits or holes are necessary to deliver the aqueous lubricant in devices using such polymers to form the lumen and outer surface of the device. In illustrative embodiments, the hydrophilic elastomers are water-swellable; e.g., in water they may swell up to 500% of their dry weight. In some embodiments, the hydrophilic elastomer of the device swells from about 20 wt % to about 500 wt % over its dry weight. In other embodiments the hydrophilic elastomer swells from about 5 wt %, about 10 wt %, about 20 wt %, about 30 wt %, about 40 wt %, or about 50 wt % up to about 100 wt %, about 150 wt %, about 200 wt %, about 300 wt %, about 400 wt % or about 500 wt % over its dry weight or over a range including any two such values. In still other embodiments, hydrophilic elastomers that swell to 600 wt %, 700 wt %, 800 wt %, 900 wt % or even 1000 wt % may be used in those devices where mechanical integrity of the device is provided by other means including non-swellable or lower swelling polymers. In certain embodiments, the hydrophilic elastomer is solid rather than having a lumen. In such devices, the matrix of polymer swells with absorbed lubricant such as glycerol or the aqueous lubricants disclosed herein.

Hydrophilic, semi-permeable elastomers useful in the present devices include without limitation hydrophilic polyurethane, hydrophilic polyether polyurethane, hydrophilic silicone polyurethane copolymer, and hydrophilic polyether polyamide. Hydrophilic polyurethanes are a class of thermoplastic or thermoset elastomers that may contain a mixture of soft blocks in the urethane that are both hydrophilic and hydrophobic. (See, e.g., Y. Gnanou, G. Hild, P. Rempp, "Hydrophilic polyurethane networks based on poly(ethylene oxide): synthesis, characterization, and properties. Potential applications as biomaterials," *Macromolecules,* 1984, 17 (4), pp 945-952.) For example, the hydrophobic soft block may be made from polyethylene oxide and the hydrophobic soft block may be polytetramethylene oxide. These soft blocks can be mixed at certain ratios known in the art to allow the polyurethane to absorb water and therefore allow water and molecules to pass across the polyurethane. Even though the polyurethane is impregnated with water, the polyurethane retains its elastomeric properties and can still function as a comfortable biomedical device. If the polyurethane is made from only a hydrophobic soft block such as polytetramethylene oxide, the resulting polymer is almost impermeable to water and would not be useful in the delivery of water slowly to vaginal cavity. In some embodiments, aliphatic diisocyanates form the urethane linkages between the block copolymers because aliphatic diisocyanates do not degrade into toxic aromatic diamines.

Hydrophilic polyurethanes include polyurethanes having ionomeric groups in the backbone of the polyurethane such as, but not limited to, carboxylic acids. (See, e.g., C W Johnston, "Hydrophilic carboxy polyurethanes," U.S. Pat. No. 4,743,673) Other ionomeric and water soluble functional groups such as urea will allow water to be imbibed into the elastomer and will allow the elastomer to swell. (See, e.g., F E Gould, "Hydrophilic polyurethanes of improved strength" U.S. Pat. No. 5,120,816.) In illustrative embodiments, the device includes a hydrophilic polyurethane selected from TECOPHILIC (a hydrophilic copolymer urethane containing both polyethylene oxide and polytetramethylene oxide soft blocks available from Lubrizol Advanced Materials, Inc., Cleveland, Ohio), HYDROTHANE (an aliphatic polyether polyurethane, available from AdvanSource Biomaterials Corp., Wilmington, Mass.), a hydrophilic styrene ethylene butylenes styrene block copolymer or hydrophilic styrene butadiene styrene block copolymer DRYFLEX (Elasto, Sweden), and polyether urethanes such as HYDROMED 640 (AdvanSource Biomaterials Corp., Wilmington, Mass.). Such hydrophilic polyurethanes may further include alkyl groups, polyethylene glycol groups, fluoroalkyl groups, charged groups (e.g., carboxylic acids, amines and the like) or other chemical groups attached to the reactive isocyanates attached to the ends of the polymer chains during synthesis (U.S. Pat. No. 5,589,563).

Hydrophilic silicone polyurethane copolymers are polymers that are a mixture of polyether segments and polydimethylsiloxane rubber (PDMS) segments copolymerized in linear block copolymers that can be melt processed. In this class of polymers there will need to be added a hydrophilic group like polyethylene oxide or segments that contain ionomeric groups so that the normally hydrophobic nature of PDMS can be counteracted so the polymer can imbibe water and deliver it through the device membrane (U.S. Pat. No. 5,756,632). Preferred embodiments use aliphatic diisocyanates to form the block copolymers.

Hydrophilic polyether polyamides include PEBAX (Arkema, Inc., France) and polyether block amide copolymers. Polyether block amide copolymers, i.e. polyamide-polyether copolymers (PAEPC), are described in U.S. Pat. No. 4,361,680 (1982) to Borg et al; U.S. Pat. No. 4,332,920 (1982) to Foy et al; and U.S. Pat. No. 4,331,786 (1982) to Foy et al. These polymers can be modified with enough hydrophilic groups like polyethylene oxide to increase their hydrophilicity and allow them to absorb water so it can be delivered through the device membrane or wall.

It will be understood by those of skill in the art that IVDs of the present technology may be manufactured using opacifiers, colors, fragrances and the like to tailor the appearance and smell of the IVDs as desired.

In some embodiments of the present devices that include a lumen, the first segment of the intravaginal device includes a hydrophobic elastomer. To allow delivery of the contents of the lumen to the outer surface, hydrophobic elastomers have at least one channel connecting the lumen to the outer surface. For example, the channels may be made by slits or holes through the elastomer forming the lumen and outer surface of the device. The slits or holes may be in any orientation on the device. In some embodiments the IVD is an IVR and the slits or holes on the ring may be, e.g., parallel to or perpendicular to the ring axis. Such slits or holes may also be employed in IVDs (including IVRs) that include hydrophilic elastomers. In some embodiments, at least one channel is closed when the elastomer is in the relaxed state and open when the elastomer is under tension.

Any hydrophobic elastomers that can be formed into biomedical grade tubing may be used in the present devices including, without limitation (non-hydrophilic) polyurethane, silicone polyurethane, silicone (polydimethylsiloxane rubber, aka PDMS), and ethylene vinyl acetate (EVA). Flexible hydrophobic elastomers such as these are well-known in the art. Suitable polyurethanes are described in Szycher's *Handbook of Polyurethanes* and *J. Biomater. Appl.* 1999 14: 67. Another flexible polymer that useful in the present devices is silicone (Silicone Elastomers 2006, International Conference, 1st, Frankfurt, Germany, Sep. 19-20, 2006 (2006), and Rubber Chemistry and Technology (2006), 79(3), 500-519 and Pujol, Jean-Marc et al. and Edited by Marciniec, Bogdan eds. From Progress in Organosilicon Chemistry, Jubilee International Symposium on Organosilicon Chemistry, 10th, Poznan, August, 1993 (1995), 503-521). Another flexible polymer that useful in the present devices is ethylene-vinyl acetate copolymer (Medical Plastics 2001, Collected Papers of the Conference and Seminar, 15th, Copenhagen, Denmark, Sep. 17-20, 2001 Pages 118-126 ISBN: 87-89753-38-0). Ethylene-vinyl acetate comes in several hardness grades that increase in hardness as the ethylene content increases. Therefore for soft and flexible vaginal devices a softer grade of ethylene-vinyl acetate is preferred.

Lubricant delivered by intravaginal devices described herein may be aqueous or non-aqueous. The aqueous lubricant can be water, hypo-osmolar water or solution, an aqueous solution, hyper-osmotic water or solution, iso-osmotic water or solution, and aqueous solution, or a gel. For example, the aqueous lubricant may be at least 90 wt % water or at least 95 wt %, at least 96 wt %, at least 97 wt %, at least 98 wt % or at least 99 wt % water, or essentially 100 wt % water. In some embodiments, the aqueous lubricant is iso-osmolar or hypo-osmolar and may include ions such as potassium, sodium, chloride and phosphate, e.g., at about 0.1 wt % to about 0.25 wt %, about 0.5 wt % or about 0.75 wt %. The aqueous lubricant may be buffered, optionally at an acidic pH to promote the natural acidity of the vagina. Thus, the present aqueous lubricants may have a pH of about 3 to about 8, from about 3 to about 6 or from about 3.5 to about 4.5 or about 4. For example, the aqueous lubricant may include vaginal fluid simulant, about 5 to about 50 mM lactic acid, an acetic acid buffer at a pH of about 3.5 to about 4.5 or to about 5.0, and optionally about 5 to about 50 mM glucose. In some embodiments, the aqueous lubricant may include vaginal fluid simulant, about 20 to about 30 mM (or about 25 mM) lactic acid, a 10 mM to about 30 mM (or about 18 mM) acetic acid buffer at a pH of about 3.5 to about 4.5 or to about 5.0 and optionally about 20 to about 30 mM (or about 25 mM) glucose. The aqueous lubricant may be free of steroids or may be free of any active pharmaceutical ingredient (i.e., those ingredients that have a therapeutic effect as opposed to a non-therapeutic biological effect).

Thus, the present aqueous lubricants may include water and a wide variety of additives such as, but not limited to, one or more salts, nonaqueous solvents (e.g., propylene glycol, glycerol), acids such as C1-8 carboxylic acids (i.e., carboxylic acids having 1-8 carbons such as, e.g., lactic acid, acetic acid), glucose, antioxidants (e.g., BHT, ascorbic acid), preservatives (e.g. sorbital, sorbic acid, parabens, EDTA, sodium benzoate, tocopherol), surfactants (e.g. polysorbate 20 or 60, sorbate salts), fragrance, flavoring agents, and sweeteners (e.g. saccharine, aspartamate). In addition, the lubricants may include pyridine, squalene, urea, complex alcohols, aldehydes, ketones, stearic acid, stearate, isopropyl palmitate, petrolatum, aloe barbadensis (Aloe Vera) leaf juice, cucumus *sativus* extract, *helianthus* annulus seed oil, soybean sterol, vitamin E acetate, vitamin A palmitate, provitamin B5, sodium acrylate/acryloyldimethyl taurate copolymer, dimethicone, glyceryl stearate, ceylalcohol, lecithin, mineral water, sodium PCA, potassium lactate, collagen, aminoacids, triethanolamine, DMDM, hydantoin, iodopropynyl, butylcarbamate, disodium EDTA, titanium dioxide. The additives may be added at a concentration such that the aqueous lubricant is hypo-osmotic, hyper-osmotic or iso-osmolar in comparison to vaginal fluids or blood or tissue. By hypo-osmotic lubricant is meant that the osmolality of the lubricant is less than that of the vaginal fluid, or blood, or tissue fluid. In contrast, a hyper-osmotic lubricant has an osmolality that is greater than that of the vaginal fluid, or blood, or tissue fluid, while an iso-osmotic lubricant roughly matches the osmolality of the vaginal fluid, or blood, or tissue fluid.

Hyper-osmotic lubricants may be aqueous or non-aqueous. Such non-aqueous lubricants may be water-soluble (i.e., at least 1 mg/mL at 25° C.). Hyper-osmotic lubricants may be prepared from appropriate concentrations of various agents including, but not limited to, glycerol, polyethylene glycol, propylene glycol, carrageenan (i.e., sulfated polysaccharides), other lubricating or hydrating substances, salts, and hyper-osmotic aqueous agents, and the like. Hyper-osmotic may lubricants include, e.g., 100% glycerol or mixtures of water and glycerol such as at least 4 wt %, about 4%, about 10 wt %, about 20 wt %, about 30 wt %, about 40 wt %, about 50 wt %, about 60 wt %, about 70 wt %, about 80 wt %, about 90 wt %, about 91 wt %, about 92 wt %, about 93 wt %, about 94 wt %, about 95 wt %, about 96 wt %, about 97 wt %, about 98 wt %, about 99 wt % glycerol, or ranges between and including any two such values. Hyper-osmotic lubricants may also include, e.g., 100% propylene glycol or mixtures of water and propylene glycol such as about 3 wt %, about 10 wt %, about 20 wt %, about 30 wt %, about 40 wt %, about 50 wt %, about 60 wt %, about 70 wt %, about 80 wt %, about 90 wt %, about 91 wt %, about 92 wt %, about 93 wt %, about 94 wt %, about 95 wt %, about 96 wt %, about 97 wt %, about 98 wt %, about 99 wt % propylene glycol, or ranges between and including any two such values. For example, the present intravaginal devices may contain or otherwise include (if solid) about 50 wt % glycerol to 99 wt % glycerol.

While not wishing to be bound by theory, it is believed that lubricant from an IVD placed in the vagina and filled with glycerol or other appropriate hyper-osmotic agent diffuses down its concentration gradient from the IVD and into the vaginal space. Because there are potentially two or more diffusing species (e.g., the osmotic agent in the device and the physiologic fluid outside the device), co-diffusion of both of these agents can occur leading to behavior that varies with time. The hyper osmotic device also attracts water from the vagina due to the low concentration of water in the device and thus a water concentration gradient is present in the system. The hydrophilic elastomer of the IVD swells with water and releases glycerol, while still attracting water into the device. Once the glycerol is present in the vaginal lumen at a concentration that is hyper-osmotic to blood, water diffuses from the bloodstream and hydrates the vaginal cavity along with the moisturizing effect of the glycerol. An additional benefit may be that the water absorbed into the polymer that was initially attracted by the glycerol (or other hyper-osmotic agent) later may act as a hydration source that could be released in response to the moisture needs of the vaginal mucosa at a later time when all of the hypo-osmotic agent has diffused from the IVD.

When the lubricant is an aqueous gel, it may include, e.g., water and one or more additives selected from the group consisting of preservatives or disinfectants (e.g., benzalkonium chloride, benzethonium chloride, benzoic acid, benzyl alcohol, boric acid, calcium lactate, glycerin, glacial acetic acid, hibitane acetate, methyl paraben, phenylethyl alcohol, potassium sorbate, propylene glycol, propyl paraben, sodium benzoate, sodium ethyl paraben, sodium propionate, sorbic acid, sorbital, tocopherol), thickening/gelling agents (e.g., agarose, aluminum magnesium silicate, carbomer, carbopol, carrageenans, dermatan sulfate, ethyl cellulose, silicon dioxide, guar gum, hydroxyethyl cellulose, hydroxyethyl methacrylate, hydroxymethyl cellulose, hydroxypropyl cellulose, hydroxypropylmethyl cellulose, maltodextran, polyacrylamide, polycarbophil, polyethylene glycol, polyethylene oxide, pluronic/poloxamer, polyvinyl alcohol, sodium alginate, sodium carboxymethyl cellulose, sodium hyaluronate, sucrose, xanthan gum), pH modifying agents (e.g., adipic acid, alkyl fumarate, aluminium sulfate, calcium acetate, calcium carbonate, calcium lactate, citric acid, glacial acetic acid, glutamic acid, glycine, hydrochloric acid, lactic acid, methionine, nitric acid, phosphoric acid, potassium bitartarate, sodium dihydrogen citrate, sodium citrate, sodium dibasic phosphate, sodium carbonate, sodium bicarbonate, sodium hydroxide, sodium lactate, sodium monobasic phosphate, stannous chloride, succinic acid, tartaric acid), surfactants/solubilizing agents (e.g., benzyl alcohol, beta cyclodextrin, polyoxyethylene 20 cetyl ether, cremophor, piperazine hexahydrate, pluronic/poloxamer, polyoxyethylene lauryl ether, lecithin, polyoxyethylene stearate, polysorbates, polyvinyl alcohol, silicone, sodium cetearyl sulfate, sodium lauryl sulfate, sorbate salts, sorbitan esters, stearic acid), antioxidants (e.g., ascorbic acid, butylated hydroxyanisole, butylated hydroxytoluene, citric acid, EDTA, phosphoric acid, sodium ascorbate, sodium metabisulfite, tartaric acid, tertiary butyl hydroquinone), emollient/emulsifier (e.g., *acacia*, allantoin, aluminium magnesium silicate, bentonite, bleached bees' wax, carbomer, polyoxyethylene 20 cetyl ether, cetostearyl alcohol, cetyl alcohol, cetyl esters wax, cetyl palmitate, cholesterol, choleth, colloidal silicon dioxide, cremophor, diglycol stearate, glycerin, glyceryl monostearate, glyceryl stearate, guar gum, hydrous lanolin, hydroxypropyl cellulose, hydroxypropylmethyl cellulose, isopropyl myristate, isopropyl palmitate, lactose, lanolin, lecithin, methyl cellulose, mineral oil, palm oil, polyoxyethylene lauryl ether, polyoxyethylene stearates, polyethylene glycol, pluronic/poloxamer, polysorbates, propylene glycol monostearate, octyl dodecanol, sodium carboxymethyl cellulose, sodium lauryl sulfate, sodium monobasic phosphate, sorbitan esters, spermaceti wax, stearic acid, stearyl alcohol, triethanolamine, petrolatum), sweetening agent (e.g., aspartamate, dextrose, maltose, mannitol, saccharine, xylitol), perfumes (e.g., isopropyl palmitate) glucose, moisturizers (e.g., aloe vera), flavoring agents, The aqueous gel lubricant may also be a water emulsion. The gel may be also in a dry form that is mounted on the ring and is hydrated in the vagina by the aqueous solution lubricant. In this case the dry gel may contain a probiotic. Probiotics are live microorganisms thought to be healthy for the host organism. According to the currently adopted definition by FAO/WHO, probiotics are: "Live microorganisms, which when administered in adequate amounts confer a health benefit on the host for example Lactic acid bacteria (LAB) or *Lactobacillus*."

The amount of lubricant (including aqueous lubricant) that may be released by the present devices may vary. For example, the present intravaginal devices may deliver 0.001 mg to about 1000 mg or even up to 2000 mg of lubricant to the outer surface of the device per day. In some embodiments the amount of lubricant delivered may be at least about 0.01 mg, about 0.1 mg, about 1 mg, about 5 mg, about 10 mg, about 25 mg, about 50 mg, about 75 mg, about 100 mg, about 250 mg, about 500 mg, about 750 mg, about 1000 mg, or about 2000 mg per day or a range between or including any two of the foregoing values. Another aspect of the present technology provides that the rate of lubricant delivered will depend on the amount of dryness or water content of the vaginal epithelium. If the vagina is wet, less lubricant will be released, and if it is dry, more will be released. This means that the amount of lubricant that is released will change over time after the initial release from the device. Functionally this is an on demand release rate based on the water content of the vaginal epithelium.

Intravaginal devices of the present technology may have a first segment that includes a tube formed from the polymer and having two ends. The ends of the first segment may be joined to each other to form, e.g., an intravaginal ring. The intravaginal devices may further include one or more additional segments, each of which comprises a polymer, an outer surface and optionally a lumen. The additional segments may contain different lubricants or other substances for delivery to the vagina. For example, a segment may contain an aqueous gel lubricant and another segment may contain an aqueous solution lubricant. Each additional segment may be separated from any adjacent segment by an polymer segment or plug. In an illustrative embodiment, the polymer segment or plug may be a hydrophobic polyurethane such as TECOFLEX or ethylene vinyl acetate. In some embodiments, the polymer of the first segment is different from the polymer of at least one additional segment. For example, the first segment may be a hydrophilic, semi-permeable elastomer and at least one additional segment may be a hydrophobic elastomer. In the present devices including more than one segment, the device may include one solid segment and one segment with a lumen. In some embodiments the segment including the lumen includes an aqueous gel lubricant. Such lubricant is delivered through perforations, slits or holes in the lumen segment. In some embodiments, the intravaginal device is refillable with aqueous lubricant.

Figure 7:
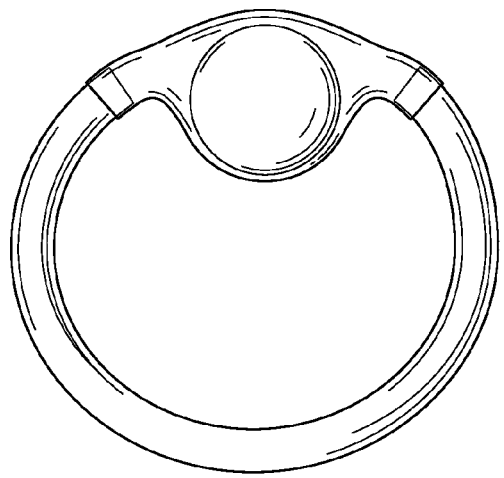
FIG. 7 illustrative embodiment of the present technology that is a matrix IVR with a lubricant containing ovule attached. The ovule contains glycerol encapsulated in gelatin.
Figure 8:
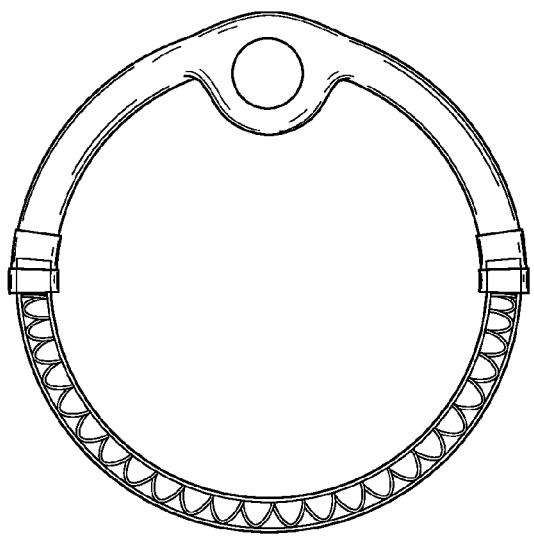
FIG. 8 illustrative embodiment of the present technology that is a dual segment IVR with a pod attached. The pod-containing segment is constructed from a solid hydrophilic elastomer. The pod may contain additional lubricant or other additives such as, e.g., probiotics. The other segment is also made of a hydrophilic elastomer but includes a lumen and is supported internally by a spring to provide extra mechanical stiffness similar to the matrix segment.

The intravaginal devices of the present technology may be designed to include one or more release chambers ("pods") for the release of additional lubricant(s) or other substances, including but not limited to drugs, as described in U.S. Ser. No. 61/375,671, filed Aug. 20, 2010 and entitled "Devices and methods for intravaginal delivery of drugs and other substances." Thus, in some embodiments, the intravaginal device further includes one or more pods loaded with an agent selected from the group consisting of drugs and probiotics such as, e.g., *Lactobacillus*, vitamins, and minerals. The pods may be located on the inner side of the ring or the outer side of the ring (See, e.g., FIGS. 2C, 2F, 6, 8). In some embodiments, the intravaginal device is an intravaginal ring having a pillow ring on the inner side of the ring. In others, the pod contains an ovule (see, e.g., FIG. 7). The ovule is a lumen containing a non-aqueous solution lubricant surrounded by a gelatin coating that dissolves when placed in the vagina. Such ovules are available as K-Y® Brand LIQUIBEADS (Johnson & Johnson Healthcare Products Division of McNeil-PPC, Inc., Skillman, N.J.).

The intravaginal devices of the present technology include a wide variety of designs. For example, the device may be an intravaginal ring. Such rings may have an outer diameter ranging from about 40 mm to about 80 mm (e.g., from about 50 mm to about 70 mm, or about 60 mm). The ring may further have a cross-sectional diameter ranging from about 3 mm, from about 5 mm, or from about 7 mm to about 10 mm or to about 12 mm, and/or an inner diameter of about 1 mm, about 2 mm, about 3 mm, about 4 mm, or about 5 mm to about 6 mm, to about 8 mm, to about 10 mm, or to about 11 mm (e.g., 8 mm). The walls of the ring may range in thickness from about 0.3 mm to about 3 mm (e.g., about 0.5 to about 1 or about 2 mm). The rings may be circular, oval, tear-drop shaped, hour-glass shaped or any other suitable shape for use in the vagina. The ring or device may have accordion-like folds that allow for extra capacity in the lumen, but sufficient structural integrity to maintain its basic shape when filled with aqueous lubricant. The intravaginal rings and devices of the present technology are flexible and may be constructed so that a force of not more than 10N is sufficient to compress the ring or device by 10%, or in some embodiments, 25%. In certain embodiments, such as, e.g., when the device is constructed from hydrophilic semi-permeable elastomers, the ring further comprises a spring configured to support the ring or any part thereof. The spring may be embedded in or inserted into the ring and encircles at least one lumen of the ring.

The most common cause of vaginal atrophy is the decrease in estrogen, which happens naturally during perimenopause, and increasingly so in post-menopause. However this condition can sometimes be caused by other circumstances and can occur throughout a woman's lifetime. The symptoms can include vaginal soreness and itching, as well as painful intercourse, and bleeding after sexual intercourse. The shrinkage of the tissues can be extreme enough to make intercourse impossible. The cause of vaginal atrophy is usually the normal decrease in estrogen as a result of menopause. Other causes of decreased estrogen levels are decreased ovarian function due to radiation therapy or chemotherapy, immune disorder, removal of the ovaries, after pregnancy, during lactation, idiopathic, and because of the effects of various medications: (Tamoxifen (Nolvadex), Danazol (Danocrine), Medroxyprogesterone (Provera), Leuprolide (Lupron), Nafarelin (Synarel)).

Accordingly, in another aspect, the present technology provides methods of lubrication, including administering an intravaginal device as described herein to a female in need of vaginal lubrication. The device may deliver any of the lubricants described herein, including aqueous or non-aqueous lubricants, e.g., water, aqueous solution, hypo-osmolar water, iso-osmolar or hyper-osmotic solution. Where the lubricant is aqueous, it may be delivered to the vaginal tissue in the form of a liquid, a vapor or a combination of both. In some embodiments of the methods, the device delivers 0.001-1000 mg or even up to 2000 mg of lubricant to the outer surface of the device per day. Other amounts of lubricant may be delivered as described herein. The lubricant may be delivered over any period of time ranging from 1 hour to 1 month. Thus, the period that the lubricant is delivered may range from 1, 2, 3, 4, 5, 10, 18, or 24 hours, or may range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. The intravaginal device may be administered to the female to relieve vaginal dryness from vaginitis, inflammation of the vagina (and the outer urinary tract) due to the thinning and shrinking of the tissues, decreased lubrication, sexual arousal disorder, menopause, drug-induced vaginal dryness, dyspareunia, sexual pain disorder, menopause, pregnancy, hormone imbalance, anxiety and diabetes, or other related disorders.

The present technology in another aspect provides method of making intravaginal devices as described herein. In one embodiment, where the device is solid, e.g., a solid hydrophilic elastomeric polymer, the elastomer may be injection molded or extruded. Where the intravaginal devices are an intravaginal ring, the extrusion molding is joined together by welding. The material is then swollen or loaded with lubricant into its final ring shape.

In some embodiments, the methods include adding a physiologically acceptable water-soluble ionic or non-ionic material to a lumen of an intravaginal device and exposing (e.g., soaking) the intravaginal device in water, wherein the intravaginal device includes a first segment having an outer surface and a lumen, wherein the first segment is configured to deliver the contents of the lumen to the outer surface, and the first segment comprises a hydrophilic, semi-permeable elastomer. The ionic material may include an alkali halide salt (e.g., NaCl, KCl) and/or other salts including but not limited to sodium acetate, potassium acetate, sodium phosphate, sodium hydrogen phosphate. The non-ionic material may include but is not limited to glycerol, polyethylene glycol, or propylene glycol.

Hyper-osmotic devices will be able to attract water or aqueous lubricant into the ring internal lumen without puncturing the lumen. The time this may take is between 1 and 24 hours depending on permeability of the membrane and the amount and nature of the osmotic attractant.

EXAMPLES

Example 1

Single Segment Tubular IVR Constructed of Hydrophobic Elastomeric Tubing with Multiple Holes Containing Aqueous Gel Lubricant A length of 6.5 mm outer diameter hydrophobic TYGON tubing (Saint-Gobain Corp., Paris, France) with a 1 mm wall thickness was formed into a ring of diameter of ~55-60 mm, by connecting the ends of the tubing with a hollow plug comprised of the same tubing material. The hollow plug dimensions were chosen as to connect the tubing ends to form a full ring structure. Small holes were drilled into the tubing along the outer annulus of the ring at ~1 cm spacings. Aqueous lubricant was loaded into the lumen via a syringe needle. Application of external force this ring (such as that which may arise from the contraction and relaxation of vaginal musculature), resulted in the expulsion of the lubricating gel (JUICY LUBE) in form of small pearls along the outer annulus of the ring as the gel migrated from the lumen through the holes and to the outer surface the tubular IVR. The same design may be constructed out of silicone or EVA medical grade tubing.

Example 2

Single Segment Tubular IVR Constructed of Hydrophobic Elastomeric Tubing with Multiple Slits Containing Aqueous Lubricant A ring of similar dimensions and construction as described in Example 1 was formed, however slits rather than holes were spaced along the inner annulus of the ring, parallel to the central ring axis. Lubricating gel (JUICY LUBE, ID LUBRICANTS, Westridge Laboratories, Inc., Santa Ana, Calif.) was loaded into the lumen via a syringe needle. Application of external force to ring results in the expulsion of the lubricating gel from the lumen through the slits to the outer surface of the inner annulus of the tubular IVR. In this design, the slits are in compression and thus closed unless a force (such as that which may arise from the contraction and relaxation of vaginal musculature) is applied to the IVR. It will be understood that slits perpendicular to the ring axis may also be placed on the inner annulus of the ring or that slits may be placed on the outer annulus of the ring in any orientation.

Example 3

Figure 3:
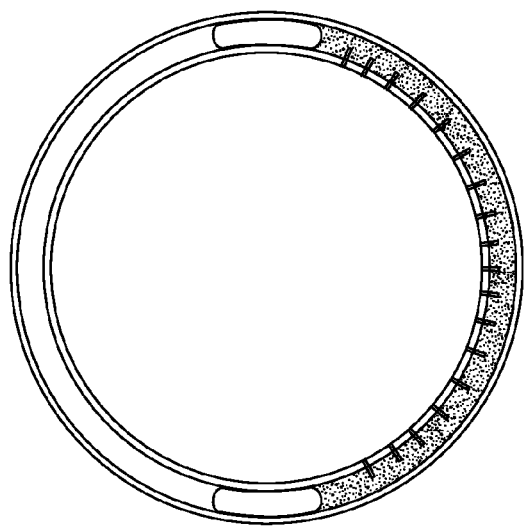
FIG. 3 shows an illustrative embodiment of the present technology that is a dual segment IVR in which each segment includes a lumen. One segment is constructed of semi-permeable hydrophilic elastomer and containing a lubricant, e.g., water. The second segment is also constructed of a hydrophilic elastomer and includes multiple slits extending from the lumen to the surface of the segment, allowing a different lubricant, e.g. gel, to be released. The ends of each segment are joined by plugs, which separate the contents of the two lumens.
Figure 4:
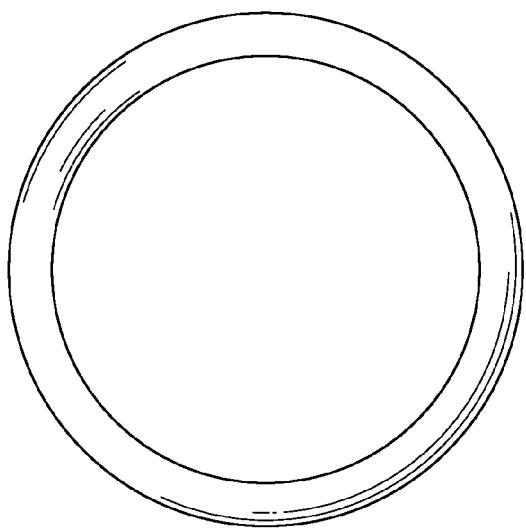
FIG. 4 shows an illustrative embodiment of the present technology that is a matrix IVR. The IVR is constructed of a single solid rod of swellable hydrophilic elastomer, by, e.g., injection molding. The matrix IVR may be "loaded" with lubricant simply by soaking in the desired lubricant for a suitable length of time.
Figure 5:
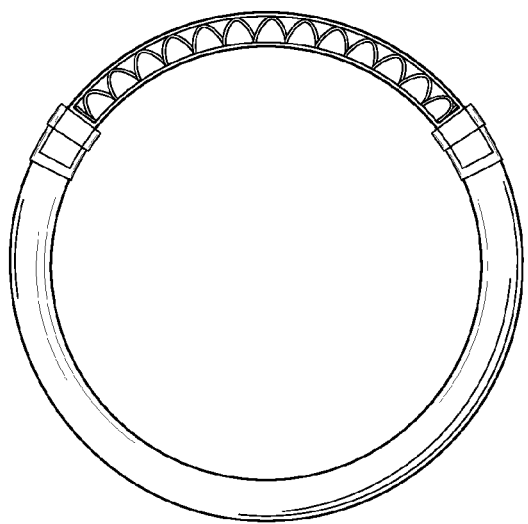
FIG. 5 shows an illustrative embodiment of the present technology that is a dual segment IVR. One segment is constructed out of a solid length of swellable hydrophilic elastomer. The other segment is also made of a hydrophilic elastomer, but includes a lumen and is supported internally by a spring to provide extra mechanical stiffness similar to the matrix segment.
Figure 6:
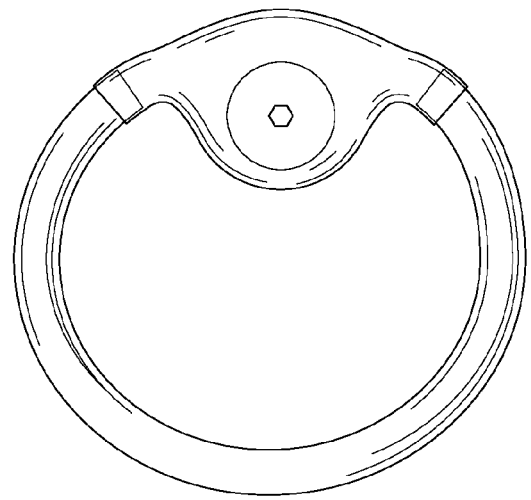
FIG. 6 illustrative embodiment of the present technology that is a matrix IVR with a pod attached. The ring portion of the IVR is constructed of a swellable hydrophilic elastomer. The pod may contain additional lubricant or other additives such as probiotics.

Single Segment Tubular IVR Constructed of Hydrophilic, Semi-Permeable Elastomeric Tubing Containing Water A tubular IVR was created employing TECOPHILIC HP-93A-100 tubing. TECOPHILIC HP-93A-100 is made of a hydrophilic, semi-permeable elastomeric polyurethane that swells to 100% of its weight when placed in water. A length of this tubing was submersed in water and the two ends of the tubing were connected each other using a connector made from polyethylene tubing that has an outer diameter that is slightly larger than the inner diameter of the TECOPHILIC tubing while still submersed in water to form a ring. When removed from the water, the water-swelled ring contained approximately 5 mL of water within the lumen. The water-swelled ring had an outer diameter of ~60 mm with a tubing outer diameter of ~8 mm. The wall thickness of the water-swelled tubing was estimated to be ~2 mm. Excess water from on the surface of the ring was removed. A line drawing of the ring is shown in FIG. 3. The surface the ring continued to remain moist as a result of permeation of the water from the lumen through the polyurethane to the outer surface of the ring. When the water-filled polyurethane ring was placed in contact with skin, a moisturizing and hydrating effect was noted. Over several days, air bubbles became visible in the lumen as a result of pressure equalization due to the continued water migration from the lumen, through the microporous holes of the polyurethane tubing and subsequent evaporation from the outer surface of the ring.

Example 4

Two Segment Tubular IVR Constructed of a Hydrophilic, Semi-Permeable Elastomeric Segment Containing Water and a Hydrophobic Elastomeric Segment with Multiple Holes Containing a Gel Lubricant To create the first segment, a first length of a hydrophobic tubing made out of TYGON, approximately 50 mm long with an outer diameter of 7 mm was plugged at each end using a small plug of molten polyurethane. Such plugs were employed to prevent/mixing of the contents upon connecting the first segment to the second segment. A second segment was created by taking a second length of tubing made of TECOPHILIC HP-93A-100, a hydrophilic, semi-permeable polyurethane elastomer. The ends of the first segment were connected to the ends of the second segment using appropriately sized hollow polypropylene tubing connectors to form a ring. Two holes, approximately 1 mm in diameter were placed parallel to the ring axis in the first segment. The first segment was filled with gel lubricant using a syringe. The second segment was filled with water, also using a syringe. The two segment tubular IVR thus constructed released both a small amount of vaginal lubricant as well as aqueous lubricant over a period of time.

Example 5

Two Segment Tubular IVR Constructed of a Hydrophilic, Semi-Permeable Elastomeric Segment Containing Water and a Hydrophobic Elastomeric Segment with Multiple Holes Containing Vaginal Lubricant As a variation to Example 4, two holes, approximately 1 mm in diameter were drilled perpendicular, rather than parallel, to the ring axis. A similar effect was achieved as in Example 4.

Example 6

Collapsible Hydrophobic Tubing

The IVR in Example 5 may be modified by employing hydrophobic tubing, which has small holes and is collapsible under vaginal pressure. Such pressure provides the force necessary to expel the vaginal lubricant from the lumen through the holes and to the outer surface the tubular IVR.

Example 7

Collapsible Hydrophobic Tubing with a Support Band

The IVR in Example 1 may be modified by incorporation of a band of flexible spring material (e.g., nylon or spring steel) into the ring, providing support to the ring as well as a retractive force useful for retention of the ring in the vaginal canal.

Example 8

Membrane-Containing IVRs, Structurally Supported

In one example the water-swellable tubing is made thin, at a wall thickness of, but not limited to, 0.1 mm to 3 mm to allow for delivery of the aqueous solution lubricant. This thin structure may not be strong enough to provide a counterbalancing force to keep the ring in the vaginal canal. Therefore, the water-swellable tubing can be stiffened using a number of support-structures that are well known in the art. In one aspect, the water-swellable tubing is extruded at a cross sectional diameter of, but not limited to, 2 mm to 10 mm and is wrapped with fiber mesh support-structure and then jacketed with another layer of molten water-swellable tubing. In another embodiment the water-swellable tubing of cross sectional diameter of, but not limited to, 2 mm to 10 mm is jacketed over a spring or a metal mesh support-structure that is made of materials including but not limited to titanium, KEVLAR, nylon, carbon fiber, stainless steel or other spring like materials or polymers that can be jacketed in a jacketing mold tool. The resulting water-swellable tubing when formed into ring would have a force to compress the IVR 10% of its initial outer diameter of, but not limited to, approximately 0.25 to 10 N. The resulting tube is cut into the correct length of, but not limited to, approximately 10 to 30 cm and formed into a ring by directly welding the water-swellable tubing ends together. In another aspect, a connector is used form a rings from the length of water-swellable tubing. The connector is a part that either jackets the water-swellable tubing or is inserted into the water-swellable tubing. The connector is welded into the water-swellable tubing making an intact and aqueous solution lubricant tight device where the aqueous solution lubricant is not leaking through the connection of the two ends of the water-swellable tubing. The weld is made by solvent welding, heat welding, induction welding, butt welding, or other thermoplastic welding techniques well known to those skilled in the art. The device is dry at this point and is filled with the aqueous solution lubricant.

In one example of filling, the aqueous solution lubricant is filled into the device at a volume of, but not limited to, 1 to 12 mL, via a syringe or similar filling apparatus that enters the device through a port built into the connector that reseals after the syringe is removed. In another embodiment the aqueous solution lubricant filling port is mounted in the water-swellable tubing.

Example 9

IVD with Check Valves

In another example the device with a thin wall would collapse due to the reduced amount of aqueous solution lubricant in the core of the device after being placed in the vagina. This problem is alleviated by adding a support-structure to the water-swellable elastomer of the device. In another example, a check valve that allows gasses into the device, but does not allow appreciable water out of the ring through the check valve, is formed into the device. In one example the check valve is assembled into the connector that connects the two ends of water-swellable tubing together in a torus shape (i.e., an IVR). In another example the check valve is mounted into the water-swellable tubing. In still another example, a piece of gas permeable membrane e.g., GORE-TEX is mounted in the connecter and allows air into the device after aqueous solution lubricant is released. In a further example, the gas permeable membrane is mounted on a hole that is formed in the water-swellable tubing.

Example 10

Rigidification of Hydrophilic Tubing

In one example the water-swellable tubing is thin, at a wall thickness of, but not limited to, 0.1 mm to 3 mm to allow for delivery of the aqueous solution lubricant. This thin structure may not be strong enough to provide a counterbalancing force to keep the device in the vaginal canal. Therefore, the water-swellable tubing can be stiffened using a number of support-structures that are well known in the art. In one aspect, the water-swellable tubing is extruded at diameter of, but not limited to, 2 mm to 10 mm and wrapped with fiber mesh support-structure and then jacketed with another layer of molten water-swellable tubing. In another embodiment the water-swellable tubing is jacketed over a spring or a metal mesh support-structure that is made materials, including but not limited to, titanium, KEVLAR, nylon, carbon fiber, stainless steel or other spring like materials or polymers that can be jacketed in a jacketing mold. The resulting water-swellable tubing when formed into ring would have a force to compress the IVR 10% of its initial outer diameter of, but not limited to, 0.25 to 10 N. The resulting tube is cut into the correct length of, but not limited to, approximately 10 to 30 cm and formed into a ring by directly welding the water-swellable tubing ends together.

In one embodiment the lumen of the device of this example is filled with water. In another embodiment, a gel forming formulation is attached to or inserted in the ring. The gel forming formulation includes polymers such as, but not limited to, hydroxyethyl cellulose, carrageenans, dermatan sulfate, hydroxypropyl cellulose, polyethylene oxide, methyl cellulose. The gel forming formulation may also include lanolin, aloe vera, moisturizers, preservatives, vitamins and probiotics or other agents known to those skilled in the art. One aspect uses a connector that is attached on the end of the water-swellable tubing and is used to form a torus from the length of water-swellable tubing. The connector is a part that either jackets the water-swellable tubing or is inserted into the water-swellable tubing. In another aspect, the connector has attached to it the ability to hold a compressed pellet of gel forming formulation. The connector is welded into the water-swellable tubing making an intact and aqueous solution lubricant tight device where the aqueous solution lubricant is not leaking through the connection of the two ends of the water-swellable tubing. The weld is made by solvent welding, heat welding, induction welding, butt welding, or other thermoplastic welding techniques well known to those skilled in the art. The device is dry at this point and is filled with the aqueous solution lubricant.

Example 11

Dual Reservoir IVR Device

An IVR was constructed containing two separate reservoirs. One reservoir was made from a hydrophilic polymer and the other from a hydrophobic polymer with pores in the elastomer. These separate reservoirs can be used to hold and release different liquids/lubricants. The first segment (hydrophilic polymer) delivered the aqueous or non-aqueous solution lubricant and the second segment (hydrophobic polymer) delivered the aqueous gel lubricant. The aqueous gel lubricant is delivered through pores in the tubing wall.

In this example, the device was fabricated from an 80 mm length of TECOFLEX EG-85A tubing segment (5.5 mm cross-section×1.5 mm wall thickness) and an 80 mm length of hydrophilic aliphatic thermoplastic polyurethane tubing segment (5.5 mm cross-section×0.7 mm wall thickness). The ends of the TECOFLEX segment were sealed using a PlasticWeld Systems, Inc. (Newfane, N.Y.) bonding die (HPS-EM; preheat 10 seconds, heat 11 seconds, cool 15 seconds, power 16%, travel distance of 3 mm). After sealing the ends, a 0.5 mm drill bit was used to drill holes along one side of the sealed tube, approximately every 3 mm starting and ending 20 mm from each end to give 20 holes. These holes were only drilled into one wall of the tube, forming a channel from the inner lumen to the surface of the tube. In other embodiments the holes can be drilled all around the rod axially so that the holes point in many directions. In another embodiment, this design can be configured as a tampon-like device. The ends of the hydrophilic aliphatic thermoplastic polyurethane segment were sealed using a bonding die (HPS-EM). By placing the clamp 9 mm from the die opening, a 6 second preheat cycle was followed by a 7 second heat cycle with a 10 second cooling cycle following. The ends of each segment were joined together using an induction welder split die (HPS-20). The ends were placed into the die, clamped, and subjected to a 25 second cycle at 50% power followed by a 12 second soak and a 20 second cooling cycle, resulting in the joining of the ends and then repeated to form the ring. During welding, the pores in the TECOFLEX segment were configured to place the drilled holes along the inner annulus of the IVR. The IVRs were annealed at 65° C. for 5 minutes and cooled at 10° C. for 20 minutes. A 27 gauge needle was inserted along the inner annulus of the IVR through the joint and into the lumen of the TECOPHILIC side. Another needle was inserted into the lumen on the other side of the joint and a 3 mL syringe was used to inject 0.5 grams of water into the IVR until the liquid started to emerge out of the other needle, thus filling the TECOPHILIC side of the IVR device. After soaking the IVR for 1 day in 100 mL of water, a 27 gauge needle and 3 mL syringe was used to inject the lumen of the TECOFLEX side with 0.1 grams of a 0.2 wt % methylene blue/K-Y® Brand Jelly (Johnson & Johnson Healthcare Products Division of McNeil-PPC, Inc., Skillman, N.J.) mixture.

In another aspect, the devices described above can be made via a multistep injection molding process where the water swellable tubing is formed into the device by methods well known to those skilled in the art.

Example 12

IVRs of Varying Shapes

The shapes of any of the IVRs of present technology can be modified as to promote increased comfort and/or to promote increased contact with the vaginal canal. For instance, the IVR may be deformed or changed from a toroid shape. Indeed, any of the examples listed are readily adaptable to cylindrical shape such as that of a tampon (see Examples 40-41 below). In one aspect, the IVR is shaped similar to an "accordion" or "bellowed" to increase the surface area of the tubing that is in contact with the vaginal epithelium. In another aspect, the shape of the IVR is elliptical, which increases comfort for the patient. In another aspect, the pods or cores are located on the outer portion of the IVR, rather than on the inner portion of the IVR. The concept of the pods or cores on the IVR are the addition of one or two or more pods or cores attached to or inserted into the IVR. The pods or cores deliver substances such as carrageenans simultaneously with the aqueous solution lubricant. In another aspect, the ring is bent out of plane to be curved, which may increase comfort to the patient and increase the surface area in contact with the vaginal epithelium. In a further aspect, the ring is the shape of an "hour-glass," which also increases the comfort to the patient. In further aspect, the IVR is prepared in the shape of a circle, with adjoining "pillows" on four sides of inner portion of the ring containing a greater quantity of aqueous solution lubricant. The dimensions of the ring are approximately 60 mm in total diameter. The outer portion of the ring containing the aqueous solution lubricant is 3 to 10 mm in diameter, and the diameter is approximately 7 mm of swollen polymer tubing. Adjoining pillows attached to four sides of the inner tubing are up 10 to 25 mm inward from the outer edge of the tubing. This would leave up to 10 mm of hollow space in the center of the "pillowed" IVR for fluid lubricant.

Example 13

Method of Insertion

In yet another aspect, the device is inserted into the vagina using a device or ring applicator (WO/1999/038468 and U.S. Pat. No. D442,688) or feminine product applicators similar to those supplied with tampons and lubricant or moisturizer products.

Example 14

Acidifying Agents in the IVR

One example of the IVR includes pH modifying agents (e.g., adipic acid, alkyl fumarate, aluminium sulfate, calcium acetate, calcium carbonate, calcium lactate, citric acid, glacial acetic acid, glutamic acid, glycine, hydrochloric acid, lactic acid, methionine, phosphoric acid, potassium bitartarate, sodium dihydrogen citrate, sodium citrate, sodium dibasic phosphate, sodium carbonate, sodium bicarbonate, sodium hydroxide, sodium lactate, sodium monobasic phosphate, succinic acid, tartaric acid) in the aqueous lubricant to promote the natural acidity of the vagina.

Example 15

Continuous Release of Aqueous Lubricant

An IVD of the present technology, e.g., an IVR, is administered to a woman in need of or desiring and a sufficient amount of the aqueous and/or non-aqueous lubricant (including, e.g., gel lubricant) is released continuously over 24 to 72 hours or up to including 5 to 7 days or up to 30 days to provide relief from vaginal dryness or vaginal discomfort. In another aspect, a sufficient amount of the aqueous lubricant (and gel lubricant) is released continuously over several minutes to several hours (up to 24 hours) to provide relief of vaginal dryness or vaginal discomfort. In another aspect, a sufficient amount the aqueous lubricant and gel lubricant is released continuously over several days (3 to 7 days) to provide relief of vaginal dryness or vaginal discomfort. In another aspect, the aqueous solution lubricant and gel lubricant is released in such a manner that it would provide sufficient relief of vaginal dryness or vaginal discomfort and be used as needed on an as needed basis from several minutes to several days. The IVD remains in place from several minutes to several days and is removed when the woman determines she has sufficient relief, or wears for as long as desired for up to several days.

Example 16

Solid Polymer Matrix IVR Constructed of TECOPHILIC SP-80A-150

1. Extrusion of TECOPHILIC SP-80A-150
Hydrophilic polymer TECOPHILIC SP-80A-150 (Lubrizol Advanced Materials, Inc., Cleveland, Ohio) was extruded to form polymer rods using methods known to those skilled in the art. Briefly, a Brabender (C.W. Brabender Instruments, Inc., South Hackensack, N.J.) single screw extruder was used to extrude approximately 200 g of TECOPHILIC SP-80A-150 (dried to 0.077% water) through a 4.5 mm rod die to give a rod of 5.5 mm cross-section. The temperatures were T1=125° C., T2=120° C., T3=120° C., T4=115° C. with a screw speed of 25 rpm.
2. Procedure for Preparing TECOPHILIC SP-80A-150 IVR Device
A matrix IVR was constructed that is capable of holding various fluids using water-swellable polymers that can hydrate (swell) up to but not limited to 150% of its dry mass, such as with TECOPHILIC SP-80A-150. Rods of TECOPHILIC SP-80A-150 (5.5 mm cross-section) were cut to 110 mm and the ends were joined by induction welding using a split die welder (HPS-20) settings of 45% power for 25 seconds followed by an 18 second soak and 20 second cool. After the joint was completed, it was allowed to cool for 10 minutes on the inside of a small beaker to support the cooling joint. After overnight storage, the rings were annealed to make the device circular by: 1) securing the rings around the cylindrical neck of a 125 mL Erlenmeyer flask and heating in a convection oven at 80° C. for 5 minutes, then air cooled at room temperature for 10 minutes.

3. Procedure for Preparing Iso-Osmolar Matrix IVR Device

A matrix IVR loaded with iso-osmolar fluid was prepared as follows. TECOPHILIC SP-80A-150 intravaginal rings (IVRs) were placed in 100 mL of 100 mM acetate buffer, containing 30 mM NaCl (pH 5, 305 mOsm) for 4 days to swell the polymer to equilibrium.

4. Procedure for Preparing Hypo-Osmolar Matrix IVR Device

A matrix IVR loaded with a hypo-osmolar fluid was prepared as follows. TECOPHILIC SP-80A-150 IVRs were placed in 100 mL of distilled de-ionized (DDI) water for 4 days to swell the polymer to equilibrium.

5. Procedure for Preparing Hyper-Osmolar Matrix IVR Device

A matrix IVR loaded with a hyper-osmolar fluid was prepared. TECOPHILIC SP-80A-150 IVRs were placed in 100 mL of a 70/30% v/v mixture of 100 mM acetate buffer with 30 mM NaCl and 3.8 M glycerol (pH 5, 428 mOsm) for 4 days to swell the polymer to equilibrium. Alternatively, glycerol could be replaced with propylene glycol.

6. Procedure for Preparing VFS Matrix IVR Device

A matrix IVR loaded with vaginal fluid simulant (VFS) was prepared as follows. To prepare 1 L of VFS, the following were combined: 5 g of glucose, 3.51 g of NaCl, 2.0 g of lactic acid, 0.4 g of urea, 0.222 g of calcium hydroxide, 0.16 g of glycerin, 0.02 g of bovine serum albumin, 1 g of glacial acetic acid, and 1.4 g of potassium hydroxide were added to DDI water. Subsequently, 5 mL of 1 M HCl was added to bring the pH to 4.21 and DDI water was then added to a 1 L volume. A TECOPHILIC SP-80A-150 IVR was placed in 100 mL of VFS for 3 days to swell the polymer to equilibrium with 3.2 mL of VFS.

Example 17

Hydrophilic Silicone Polyurethane Matrix IVR

The purpose of the following prototype was to construct an IVR out of a silicone material. In this embodiment, segments of hydrophilic silicone polyurethane (DSM Biomedical, Berkeley, Calif.) rod were cut to 155 mm (5.2 mm cross-section). The ends were joined by butt welding the segments together (max power, 8 second melt time) to form a ring. The resultant flashing was removed from the polymer ring after curing overnight.

Example 18

TECOPHILIC HP-93A-100 Matrix Device with Pod Holder

An IVD was constructed combining a swellable polymer matrix IVR with a non-swellable elastomeric section to hold a pod. A pod is a polymeric chamber that has at least one orifice through which a formulation is released when in contact with the vaginal cavity. The chamber contains a sustained release formulation, wherein the formulation includes a water-swellable polymer and an intravaginally administrable substance. By "sustained release formulation" is meant a formulation of the intravaginally administrable substance that is released over the course of a period of one or more hours up to several days. A 30 mm segment, including the pod holder, was cut out of an injection molded TECOFLEX EG-85A pod holder. A TECOPHILIC HP-93A-100 rod (cross-section 4.6 mm) was cut to 105 mm. The TECOPHILIC polymer segment was annealed, to form a ring shape with high circularity at 70° C. for 5 minutes inside of a 100 mL beaker, and then cooled at room temperature (RT) for 15 minutes to provide initial curvature to the segment. A ring was formed by butt-welding (max power, 8 seconds of melting) the ends of the TECOPHILIC rod to the ends of the TECOFLEX pod holder segment.

Example 19

TECOPHILIC HP-93A-100 Reservoir Device with Pod Holder

The present device combines a swellable reservoir IVR with a non-swellable section to hold a pod. An injection molded TECOFLEX EG-85A pod holder IVR was cut in half so each half included a pod holder and was 80 mm in length. TECOPHILIC HP-93A-100 tubing (cross-section of 4.8 mm and wall thickness of 250 µm) was cut to 76 mm. A stainless steel spring (4.01 mm cross-section, 0.51 mm wire diameter, 3 coils/cm) was cut to 80 mm. 5 mm of the Tecophilic tubing was overlapped onto the TECOFLEX rod and then wrapped in a 5 mm wide, 80 mm long piece of aluminum foil to increase the cross-section to 5.5 mm. The joint was placed in an induction welder at 45% power for 25 seconds followed by an 8 second soak and a 10 second cool to join the tubing to the rod. The spring was inserted into the tube and compressed so the other end of the tube could be overlapped onto the rod and the procedure from above was repeated to form a ring. Removal of the aluminum foil resulted in a complete IVR.

Example 20

*Lactobacillus* Pods

In the present example, pods were constructed out of acrylonitrile butadiene styrene (ABS) for the purpose of holding and releasing pellets made of materials such as *Lactobacillus*. The pods were inserted into matrix and reservoir IVDs having pod holders (described above in Examples 18 and 19). Pellets were made from powder contained in Natural Factors (Coquitlam, BC, Canada), Multi *Acidophilus* capsules. Approximately 170 mg of the powder was pressed into a pellet of 4.6 mm height×6 mm diameter for 1.5 minutes at 5000 lbs of pressure using a manual bench top press (Carver Inc., Wabash, Ind.). ABS pods were fabricated on a lathe by using ¼inch ABS rod stock with interior dimensions of 5.8 mm height and a diameter of 6.5 mm. The pellets were inserted into these pods and ABS lids or caps with a 1.5 mm orifice were glued onto the pods using ABS cement, which sealed the pellet inside. A pod was inserted into a matrix pod holder and a reservoir pod holder for release studies Example 21

IVR with Matrix Pod Holder and 100% *Lactobacillus* Pellet

An IVR was constructed that combines a water-swellable section and a non-swellable section holding and releasing a *Lactobacillus* pellet. A TECOPHILIC HP-93A-100 matrix pod holder IVR (described earlier) was used. Approximately 170 mg of the inside powder from Natural Factors Multi

*Acidophilus* capsules was pressed into a pellet of 4.6 mm height×6 mm diameter for 1.5 minutes at 5000 lbs of pressure using a manual bench top press. A *Lactobacillus* pellet (6 mm in diameter×4.6 mm in height, 0.1717 g) was glued into a circular hole in the elastomer made by injection molding using the TECOFLEX 1-MP adhesive. Only one of the exposed, circular sides of the cylindrical pellet was coated with glue. An identical device has been fabricated with a removable adhesive strip covering the pellet to prevent leaking or dispensing of the contents in the device prior to use.

Example 22

HPC/*Lactobacillus* Pellet/Pod

An IVR was constructed that can release *Lactobacillus* from a pod. The pod was made out of ABS and holds and releases material that is in the form of a pellet composed of a HPC/*Lactobacillus* mixture. In this embodiment, pellets were made by combining Klucel GF Pharm hydroxypropyl cellulose (HPC) (Hercules Inc., Wilmington, Del.) with the powder obtained from Natural Factors Multi *Acidophilus* capsules (50/50 wt %). Approximately 170 mg of the powder was pressed into a pellet of 4.6 mm height×6 mm diameter for 1.5 minutes at 5000 lbs of pressure using a manual bench top press. The pellets were inserted into ABS pods with interior dimensions of 5.8 mm height and 6.5 mm diameter. ABS lids, with a 1.5 mm orifice were glued onto the pods using an ABS cement to seal the pellet inside. A pod was inserted into a matrix pod holder (of Example 18) and reservoir pod holder (of Example 19) for release studies. An identical device has been fabricated with a removable adhesive strip covering the pod to prevent leaking or dispensing of the contents in the pod prior to use.

Example 23

HEC Pellet/Pod Device

In the present example, pods were constructed out of ABS for the purpose of holding and releasing pellets made of materials such as hydroxyethyl cellulose (HEC) lubricant were constructed out of ABS. Pellets were made from 1 wt % Rhodamine B Isothiocyanate-Dextran and 99 wt % Natrasol™ 250 HX hydroxyethyl cellulose (HEC). Approximately 170 mg of the powder was pressed into a pellet of 4.6 mm height×6 mm diameter for 1.5 minutes at 5000 lbs of pressure using a manual bench top press (Carver Inc., Wabash, Ind.). Pellets also were made from 100 wt % Natrasol™ 250 HX hydroxyethyl cellulose using an identical method. The pellets were inserted into ABS pods with interior dimensions of 5.8 mm height and 6.5 mm diameter. ABS lids with a 1.5 mm orifice were glued onto the pods using an ABS cement to seal the pellet inside. A pod was inserted into a matrix pod holder (of Example 18) and a reservoir pod holder (of Example 19) for release studies. An identical device has been fabricated with a removable adhesive strip covering the pellet to prevent leaking or dispensing of the contents in the device prior to use.

Example 24

K-Y® Brand LIQUIBEADS® in Matrix Pod Holder Device

In the present example, a glycerin ovule such as the K-Y® Brand LIQUIBEADS® ovule was mounted in a matrix pod holder IVR. A Tecophilic HP-93A-100 matrix pod holder IVR (of Example 18) was used. The pod holder was stretched over a 10 mm Allen Wrench and annealed in an oven for 5 minutes at 100° C. The pod holder was then stretched over a 5 mL scintillation vial and placed in the oven for 5 minutes at 100° C. After cooling at room temperature for 20 minutes, a K-Y® Brand LIQUIBEADS® ovule was inserted into the pod holder.

Example 25

TECOPHILIC HP-60D-35 Reservoir Device Filled with Glycerol

A reservoir IVR filled with glycerol was constructed as follows. The intravaginal rings were constructed using hydrophilic aliphatic thermoplastic polyurethane TECOPHILIC HP-60D-35 tubing with a cross-section of 4.8 mm and a wall thickness of 1.10 mm. The tubing was cut to a length of 170 mm and both ends were sealed using a tip-forming die. Since the cross-section of the tubing was smaller than the 5.5 mm inner diameter of the bonding die clamps, the air that pressurizes the clamps was disabled The unpressurized clamps were still used to support and guide the tubing into the die. By placing the clamp 1 cm from the die opening, a 10 second preheat cycle was followed by an 11 second heat cycle, with the tubing manually fed into the die opening after the 10 second preheat cycle. A 15-second cooling cycle followed and resulted in a 2-3 mm tip. After sealing both ends, an induction welder was used to join the ends together to form a ring. The ends were placed into the die, clamped, and subjected to a 27 second cycle at 45% power, which was followed by an 18 second soak and a 15 second cooling cycle. Alternatively, glycerol could be replaced with propylene glycol.

Example 26

Hydrophilic Thermoplastic Aliphatic Polyurethane Lumen Devices (0.7 mm Wall Thickness)

A reservoir IVR constructed out of hydrophilic thermoplastic aliphatic polyurethane (DSM Biomedical, Berkeley, Calif.), similar to TECOPHILIC HP-60D-35 (5.5 mm cross-section×0.7 mm wall thickness) was cut to 169 mm and the ends sealed using a bonding die (HPS-EM; preheat 6 seconds, heat 7 seconds, cool 10 seconds, power 20%, travel distance of 9.0 mm). After sealing, the ends were welded together using an induction welder (25 seconds of 55% power, 15 second soak, 15 second cool). After curing overnight, two 27 gauge needles were inserted through the joint into the lumen. In another embodiment the syringe needles were inserted through the inside wall of the torus, which is under compression. A syringe filled with various liquids described in Examples 28, 29 and 31 below was used to fill the lumen with the mixture through one syringe needles. In one embodiment TECOFLEX 1-MP adhesive was used to seal the syringe needle holes after filling.

Example 27

Hydrophilic Thermoplastic Aliphatic Polyurethane Lumen Devices (1.5 mm Wall Thickness)

A reservoir IVR constructed out of hydrophilic thermoplastic aliphatic polyurethane, similar to TECOPHILIC HP-60D-35 (5.5 mm cross-section×1.5 mm wall thickness) was cut to 169 mm and the ends sealed using a bonding die (HPS-EM; preheat 10 seconds, heat 11 seconds, cool 15 seconds, power 16%, travel distance of 4.0 mm). After sealing, the ends were welded together using an induction welder (25 seconds of 55% power, 15 second soak, 15 second cool). After curing overnight, two 27 gauge needles were inserted through the joint into the lumen. In another embodiment the syringe needles were inserted through the inside wall of the torus, which is under compression. A syringe filled with various lubricants as described in Examples 30 and 32 below was used to fill the lumen with the mixture through one syringe needles. In one embodiment TECOFLEX 1-MP adhesive was used to seal the syringe needle holes after filling.

Example 28

70 wt % Glycerol/30 wt % Water Hydrophilic Thermoplastic Aliphatic Polyurethane (0.7 mm Wall Thickness) Reservoir Device A reservoir IVR containing a mixture of glycerol and water was constructed as described. The device from Example 26 was filled with a 70/30 wt % water/glycerol mixture using the syringe method from Example 26. Alternatively, glycerol could be replaced with propylene glycol.

Example 29

100% Glycerol-Filled Hydrophilic Thermoplastic Aliphatic Polyurethane (0.7 mm Wall Thickness) Reservoir Device A reservoir IVR containing glycerol was constructed as described. The device from Example 26 was filled with 100% glycerol using the syringe method from Example 26.

Example 30

100% Glycerol-Filled Hydrophilic Thermoplastic Aliphatic Polyurethane (1.5 mm Wall Thickness) Reservoir Device A reservoir IVR containing glycerol was constructed as described. The device from Example 27 was filled with 100% glycerol using the syringe method from Example 27.

Example 31

DDI Water-Filled Hydrophilic Thermoplastic Aliphatic Polyurethane (0.7 mm Wall Thickness) Reservoir Device A reservoir IVR containing DDI water was constructed as described. The device from Example 26 was filled with DDI water using the syringe method from Example 26.

Example 32

DDI Water-Filled Hydrophilic Thermoplastic Aliphatic Polyurethane (1.5 mm Wall Thickness) Reservoir Device A reservoir IVR containing DDI water was constructed as described. The device from Example 27 was filled with DDI water using the syringe method from Example 27.

Example 33

Remote Loaded NaCl Reservoir Device

A reservoir IVR filled with water and fabricated without puncturing or perforating the wall of the device was constructed. IVRs was prepared using tubing made from TECOPHILIC HP-93A-100 with a cross-section of 4.8 mm and a wall thickness of approximately 250 µm cut to a length of 120 mm. The same polymer in the form of a solid rod of 4.6 mm cross-section was cut into 20 mm segments to be used as plugs to seal the tube. One plug was inserted 10 mm into one end of the tube and then 0.3784 and 0.6873 grams of NaCl was placed into each device, respectively. After the NaCl addition, the other end of the plug was inserted into the open end of the tube until the two ends of the tube were joined together, forming a closed system. An induction welder was used to join the ends of the tube together and join them onto the plug. The plug was placed into the die, clamped, and subjected to a 25 second cycle at 45% power followed by an 8 second soak and a 10 second cooling cycle. After curing overnight, the IVRs were placed in 250 mL of DDI water at 37° C. After 5 days, the IVRs had increased in mass by approximately 2.5 grams and the inside was filled with the liquid. Sampling the remaining fluid exterior to the IVR (filled with 0.6873 g of NaCl) after 7 days of soaking, the osmolality was found to be 62 mOsm, making this IVR hypo-osmotic to blood plasma. Adjusting the amount of NaCl added to the interior or the amount of water the IVR is placed in to soak, the final, equilibrium concentration of NaCl is used to create a hyper-osmotic, iso-osmotic, or hypo-osmotic interior lumen of the IVR relative to the body.

Example 34

A 97/3 wt % Water/Glycerol Reservoir (Remote Loading Method)

An IVR filled with a mixture of glycerol and water loaded into the IVR without creating a hole in the membrane by puncturing with a syringe. IVRs were constructed using tubing made from TECOPHILIC HP-93A-100, with a cross-section of 4.8 mm and a wall thickness of approximately 250 µm cut to a length of 120 mm. To load the tubing with glycerol, 0.8 grams of glycerol was placed into each sample of tubing along with a custom compression spring (120 mm long, 4.01 mm cross-section, 0.51 mm wire, 3 coils/cm). A solid rod of TECOPHILIC HP-93A-100 of 4.6 mm cross-sectional diameter was cut into 20 mm segments to be used as plugs to seal the tube ends. A closed ring or tube is formed by inserting a 10 mm polymer plug into the two open ends of the tubing and joining the ends together. A 1 cm wide×80 mm long piece of aluminum foil was wrapped around the joint to increase the cross-section to 5.5 mm so it would fit into the welder. An induction welder was used to join the ends of the tube together and join them onto the plug. The plug was placed into the die, clamped, and subjected to a 25 second cycle at 45% power followed by an 8 second soak and a 10 second cooling cycle. After curing overnight, the IVRs were placed in 20 mL of DDI water at 37° C. After 2 days, the IVRs had increased in mass by 2-2.3 grams and the inside (lumen) was filled with liquid, which was a mixture of 97 wt % water/3 wt % glycerol. Increasing/decreasing the amount of glycerol added to the interior or increasing/decreasing the amount of water the device is immersed in will influence the final ratio of glycerol to water, as well as osmolality of the final solution. The device also could be placed in a mixture such as water and glycerol to soak. This will load water and glycerol into the device. Alternatively, the device is placed into water for an initial soaking and then placed in glycerol or another mixture to draw glycerol into the device, as well.

Appropriate agents also may be used to create an osmotic gradient to load the IVRs with aqueous fluid lubricant using agents including, but not limited to, glycerol, polyethylene glycol, propylene glycol, carrageenan (i.e., sulfated polysaccharides), other lubricating or hydrating substances, salts, and osmotic aqueous agents, etc.

Example 35

DDI Water Reservoir Device

A reservoir IVR filled with DDI water was constructed as follows. Devices filled with a hypo-osmotic solution (e.g., water with little or no additives) were constructed and demonstrated controlled delivery of water. In the embodiment described below, the hyper-osmotic vaginal fluid solution in the vaginal cavity osmotically attracts the water or water vapor from the IVR in a manner that delivers the water from the IVR slowly over a period of time (i.e., several days (1-5 days) and potentially up to 30 days). The IVRs were constructed using tubing made from TECOPHILIC HP-93A-100 with a cross-section of 4.8 mm and a wall thickness of ~250 μm cut to a length of 120 mm. The same polymer as a solid rod of 4.6 mm cross-section was cut into 20 mm long segments to be used as plugs to seal the tube. Inserting one end of the plug 10 mm into the tube, a compression spring (120 mm long, 4.01 mm cross-sectional width, 0.51 mm OD wire, 3 coils/cm) was inserted into the tube and the other end of the plug was inserted into the opened end of the tubing to form a closed tube. (In another example, the spring/support was omitted from the device.) An induction welder was used to join the ends of the tube together and fuse them onto the plug. The plug with tubing over it was placed into the die, clamped, and subjected to a 25 second cycle at 45% power followed by an 8 second soak and a 10 second cooling cycle. After curing overnight, a 27 gauge needle was inserted along the inner annulus of the IVR through the joint and into the lumen. Another needle was inserted into the lumen on the other side of the joint. In another embodiment the syringe needles were inserted through the inside wall of the torus under compression. A 3 mL syringe was used to inject approximately 1.5 grams of double distilled (DDI) water into the IVR until the water started to come out of the other needle, filling the IVR with liquid. The IVRs were placed in 100 mL of DDI water with the needles left in place, allowing the polymer to reach equilibrium swelling.

Example 36

Multi-Lumen: Matrix/Reservoir

An IVD was constructed as follows using two different types of liquid/lubricant reservoirs: a solid and a hollow, or matrix and reservoir, respectively, each holding a different type of liquid/lubricant. TECOPHILIC HP-93A-100 tubing (cross-sectional diameter of 4.8 mm and wall thickness of 250 μm) was cut to 40.5 mm. TECOPHILIC HP-93A-100 polymer rod (cross-section 4.6 mm) was cut to 91.5 mm. The rod section was annealed at 70° C. for 5 minutes inside of a 50 mL beaker, then air cooled at room temperature to give a circular final product. A stainless steel spring (4.01 mm cross-section, 0.51 mm wire diameter, 3 coils/cm) was cut to 38.45 mm. A 5 mm section of the TECOPHILIC HP-93A-100 tubing was overlapped onto the TECOPHILIC HP-93A-100 rod and then wrapped in a 3 mm wide×80 mm long piece of aluminum foil to increase the cross-section to 5.5 mm. The resultant joint was induction welded using a split-die welder (HPS-20; PlasticWeld Systems, Inc.) at 45% power for 25 seconds followed by an 8 second soak and a 10 second cool to join the tubing to the rod. The spring was inserted into the open end of the tube and compressed to allow the other end of the tube to overlap onto the other end of the TECOPHILIC HP-93A-100 rod and then wrapped in a 3 mm wide×80 mm long piece of aluminum foil to increase the cross-section to 5.5 mm. The resultant joint was induction welded using a split-die welder (HPS-20; PlasticWeld Systems, Inc.) at 45% power for 25 seconds followed by an 8 second soak and a 10 second cool to join the tubing to the rod, forming a complete ring. A 27 gauge needle was inserted through each joint into the lumen of the tubing section and a 3 mL syringe was used to fill the lumen with glycerol through one needle while air escaped from the other needle. In one embodiment TECOFLEX 1-MP Adhesive (Lubrizol Advanced Materials, Inc., Cleveland, Ohio) was then used to seal the needle holes after filling.

Example 37

TECOFLEX EG-85A Reservoir Device with Holes/Pores

A reservoir IVR was constructed out of a hydrophobic polymer with pores allowing the release of loaded lubricant/liquid. TECOFLEX EG-85A tubing (5.5 mm cross-section× 1.5 mm wall) was cut to 159 mm and the ends were sealed using a bonding die (HPS-EM; preheat 10 seconds, heat 11 seconds, cool 15 seconds, power 16%, travel distance of 3 mm). After sealing the ends, a 0.5 mm drill bit was used to drill holes along one side of the sealed tube, approximately every 3 mm starting and ending 20 mm from each end to give 40 holes in the rod segment. The holes were only drilled into one wall of the tube, forming a channel from the inner lumen to the surface of the tube. After drilling the holes, the ends were welded together using an induction welder (25 seconds of 37% power, 12 second soak, 15 second cool) in a configuration placing the drilled holes along the inner annulus of the IVR. A 27 gauge needle and 3 mL syringe was used to inject the lumen of the TECOFLEX EG-85A side with 0.1 grams of a 0.2 wt % methylene blue/K-Y® Brand Jelly mixture. An identical device has been fabricated with a removable adhesive strip to prevent leaking of the contents in the device prior to use.

Example 38

Dual Reservoir IVR Device with Polymer Plugs Separating the Reservoir Chambers

An IVR containing two separate reservoirs was constructed from a hydrophilic elastomer with a hydrophobic polymer separating the two reservoirs. These separate reservoirs can be used to hold and release different liquids/lubricants. In this embodiment, the device was fabricated from two 80 mm length of hydrophilic aliphatic thermoplastic polyurethane tubing segment (5.5 mm cross-section×0.7 mm wall thickness). The ends of the hydrophilic aliphatic thermoplastic polyurethane segment were sealed using a bonding die (HPS-EM). By placing the clamp 9 mm from the die opening, a 6 second preheat cycle was followed by a 7 second heat cycle with a 10 second cooling cycle following. Two 5 mm long segments (5.5 mm cross-section) of TECOFLEX EG-85A were cut to act as separators/connectors. These connectors have the property of not allowing the aqueous solution lubricant from the first segment into the second segment forming two independent volumes. A Fenner Drives (Mannheim, Pa.) polyurethane butt welding kit was used with maximum power to melt the TECOFLEX EG-85A segments on the ends of the tubing segments. These ends were then melted together using the same procedure to produce an IVR. A 27 gauge needle was inserted along the inner annulus of the IVR through the joint and into one lumen. Another needle was inserted into the lumen on the other side of the joint and a 3 mL syringe was used to inject 0.8 grams of water into the IVR until the liquid started to emerge out of the other needle. The same procedure was repeated with the other chamber except 0.8 g of a 70/30 wt % glycerol/water mixture was used. In one embodiment TECOFLEX 1-MP adhesive was used to seal the syringe needle holes after filling.

Example 39

Tampon-Shaped Reservoir Device

The present example demonstrates an alternative design for a lubricating device. In this embodiment, TECOPHILIC HP-93A-100 tubing (10.1 mm cross-section×1.56 mm wall thickness) was cut to 60 mm. Approximately 2 mm of each end of the tube were lightly clamped between two aluminum plates at 145° C. for 20 seconds to seal each end of the tube. A 27 gauge needle was inserted on either end of the tube and a syringe was used to inject glycerol into the tube through one of the needles. In one embodiment, 1-2 cm of each end of the tube was then dipped into approximately 50 mg of TECOFLEX 1-MP adhesive to seal the needle holes. An "unglued" length of 3 cm remained.

Example 40

Dual Reservoir Tampon Device

The present example demonstrates an alternative design for a lubricating device with two different reservoirs delivering different lubricants. Two 30 mm segments of TECOPHILIC HP-93A-100 tubing (9.53 mm cross-section with 1.4 mm wall thickness) were cut. A TECOFLEX EG-85A plug (7 mm cross-section, 5 mm long) was inserted into the end of each tube and a Fenner Drives polyurethane butt welding kit was used with maximum power to melt the plugs into the end of each tube, sealing the tube. After sealing each tube, one end was joined to another end using the same procedure to produce an approximately 60 mm long dual reservoir device. A 27 gauge needle was inserted through the joint and into one lumen of the device. Another needle was inserted into end of the device and a 3 mL syringe was used to inject 0.8 grams of water into the IVR until the liquid emerged out of the other needle, thus filling one of the chambers. The same procedure was repeated with the other chamber except 0.8 g of a 70/30 wt % glycerol/water mixture was used. In one embodiment TECOFLEX 1-MP adhesive was used to seal the syringe needle holes after filling. One could make a tampon-shaped device with any combination of solid or hollow sections/lumens similar to the multi-lumen IVR devices that have been prepared.

Example 41

100 wt % Water-Swellable Polyurethane Device

Water swellable polyurethane HP-93A-100 was extrusion molded on a Haake Minilab (Thermo Electron Corporation, Newington, N.H.) extruder into a cord that was 5.5 mm in cross sectional diameter and about 155 mm long. The device was welded using induction welding into a ring shape and annealed on a glass cone for 30 minutes at 70° C. The resultant device was measured and swelled in 300 mL vaginal fluid simulant (90.6 mM sodium chloride, 25.6 mM sodium lactate and 17.7 mM acetic acid). Over two days the device swelled to its equilibrium mass that was approximately two times its initial mass. When placed in the air the device would provide moisture to surfaces it was in contact with and would feel moist to the touch, as well as lose mass in the form of moisture to the ambient atmosphere.

Example 42

Matrix and Reservoir Tampon Device

The present example demonstrates an alternative design for a lubricating device with a reservoir section and a matrix section delivering lubricants. A segment of TECOPHILIC HP-93A-100 tubing (cross-sectional diameter of 4.8 mm and wall thickness of 250 μm) was cut to 30 mm. TECOPHILIC HP-93A-100 polymer rod (cross-section 4.6 mm) was cut to 30 mm. The TECOPHILIC HP-93A-100 rod section was inserted 10 mm into the end of the tubing section and then wrapped in a 3 mm wide×80 mm long piece of aluminum foil to increase the cross-section to 5.5 mm. The resultant joint was induction welded using a split-die welder (HPS-20Y) at 45% power for 25 seconds followed by an 8 second soak and a 10 second cool to join the tubing to the rod. A 5 mm long section of TECOPHILIC HP-93A-100 rod was inserted into the other, open end of the tubing section and then wrapped in a 3 mm wide×80 mm long piece of aluminum foil to increase the cross-section to 5.5 mm. The resultant joint was induction welded using a split-die welder (HPS-20; PlasticWeld Systems, Inc., Newfane, N.Y.) at 45% power for 25 seconds followed by an 8 second soak and a 10 second cool to join the tubing onto the 5 mm rod section, sealing the tubing section. A 27 gauge needle was inserted through the joint and into the lumen of tubing section. Another needle was inserted into end of the device and a 3 mL syringe was used to inject 0.2 grams of water into the IVR until the liquid emerged out of the other needle, thus filling the lumen. In one embodiment TECOFLEX 1-MP adhesive was used to seal the syringe needle holes after filling. After the TECOFLEX 1-MP adhesive had cured for 10 minutes, the device was submerged in 50 mL of water to soak/swell the rod/matrix section of the device. After soaking for 24 hours, the rod/matrix section had swollen with 0.45 g of water.

BIOLOGICAL EXAMPLES

Example 43

Procedures for In Vivo Sheep Studies

In vivo efficacy studies using a sheep animal model were performed using selected IVRs designed to demonstrate delivery of fluid or lubricants in an animal model. The purpose of these studies was to measure the amount of fluid found in the sheep vaginal lumen released from or in response to various selected IVR designs. The designs described above used in the sheep model include iso-osmolar, hypo-osmolar, and hyper-osmolar solution containing IVRs such as: 1) iso-osmolar acetate buffer matrix IVR (Example 16.3), 2) 97/3 wt % water/glycerol reservoir IVR (Example 34), 3) 70/30 wt % acetate buffer/glycerol matrix IVR (Example 16.5), 4) 100% glycerol reservoir IVR (Example 25), 5) 70/30 wt % glycerol/water reservoir IVR (Example 28), 6) DDI water reservoir IVR (Example 35), 7) DDI water matrix IVR (Example 16.4), 8) naïve/baseline data (no IVR, naïve control), and 9) aliphatic thermoplastic polyurethane (PU) IVR (placebo control IVR). Naïve/baseline data and placebo IVR data were obtained using N=6 animals for up to 5 consecutive days for each animal Each IVR design (N=3) was pre-weighed and placed approximately 6-9 cm into the sheep vaginal canal (placed consistently in the vaginal canal near the cervix). Each IVR design remained in the sheep vagina up to a 5 day period.

Example 44

Weck-Cel® Procedure to Determine Vaginal Fluid Amount

To determine the amount of fluid released from or generated as a result of the IVR design, for each sample, a spear-tipped Weck-Cel® (Medtronic Inc., Fridley, Minn.) swab attached to a custom made gel applicator apparatus was placed onto the vaginal epithelial mucosa at approximately 6 cm into the vagina for 2 minutes and held parallel to the floor to ensure contact with the vaginal epithelia mucosa. The spear-tipped Weck-Cel® swab readily absorbs up to approximately 400 µl of water or aqueous fluid. The Weck-Cel® swab measurements were made at 6 hours and up to 1, 2, 3, 4, and 5 days. Weck-Cels® swabs were weighed prior to and immediately following each sample time point to determine the amount of fluid collected, as a result of the fluid released or generated in the vaginal canal. The collected Weck-Cel® swab weights were compared to multi-day naïve/baseline and placebo IVR data for each group of sheep. For statistical assessment, Student's two-tailed t-test with unequal variance and sample size was used to test the statistical significance of the change in Weck-Cel® swab weight ($\alpha=0.05$) in comparison to the placebo Weck-Cel® swab change in swab weight measurements. The results are shown in Table 1. The hypo-osmotic IVR designs show a daily increase in Weck-Cel® fluid collection of approximately 70% to 220% of placebo measurements. Importantly, for the two hyper-osmotic IVR designs, 100% glycerol reservoir IVRs (Example 25) and 70/30 wt % glycerol/water reservoir IVRs (Example 28), the Weck-Cel® swab results show a statistically significant ($\alpha=0.05$, Student's two-tailed t-test) increase in daily vaginal fluid levels over the placebo control measurements for the up to 5 day test period. The hyper-osmolar solution containing IVRs (both 100% glycerol reservoir IVRs and 70/30 wt % glycerol/water reservoir IVRs) showed a daily increase of approximately 360 to 470% of placebo fluid levels collected using the Weck-Cel® method.

TABLE 1

The in vivo Weck-Cel ® swab sheep results.

| | Weck-Cel ® Mass | |
|---|---|---|
| IVR Design | Mass change (mg) | % of placebo mass (%) |
| Hypo-osmolar IVRs | | |
| Acetate Buffer Matrix | 27 ± 20 | 118 ± 88 |
| 97% Water/3% Glycerol Reservoir | 50 ± 17 | 221 ± 74 |
| DDI Water Reservoir | 37 ± 10 | 162 ± 45 |
| DDI Water Matrix | 16 ± 6 | 69 ± 26 |
| Hyper-osmolar IVRs | | |
| 70% Acetate Buffer/30% Glycerin Matrix | 81 ± 30 | 359 ± 131 |
| 100% Glycerin Reservoir | 81 ± 19* | 358 ± 84* |
| 70% Glycerin/30% Water Reservoir | 106 ± 26* | 471 ± 113* |

Data are mean ± SEM (*$p < 0.05$ compared with placebo IVR control data, Student's two-tailed t-test with unequal variance and sample size). The naïve/baseline data resulted in a mean Weck-Cel ® mass of 11 ± 6 mg. The placebo IVRs resulted in a mean Weck-Cel ® mass of 23 ± 24 mg. Positive values indicate an increase in mass of the Weck-Cel ® swab.

Example 45

Post-Study Difference in IVR Weight (Mass) to Determine Fluid Release from IVRs in Sheep A second method of monitoring the effect of the IVR device involved weighing the IVRs before and after placing them in the sheep vaginal lumen for 5 days. A reduction (negative change) in weight indicated fluid release from the IVR as shown in Table 2. After the final measurement time point, the IVRs were removed and cleaned with a 70/30 v % isopropyl alcohol/water solution to eliminate any surface substrate (i.e., residual mucous) and weighed to determine the fluid weight change of the IVR following exposure to the sheep vaginal epithelial mucosa for up to 5 days. The hypo-osmolar devices (97/3 wt % water/glycerol reservoir, DDI water reservoir, DDI water matrix) and the iso-osmolar IVR (Acetate Buffer matrix) delivered between 100 to 900 milligrams (approximately 100 to 900 µl) of fluid over the up to 5 day period tested, thus indicating effective delivery of fluid. Student's two-tailed t-test with unequal variance and sample size ($\alpha=0.05$) was used to compare the change in IVR mass to the change in placebo IVR mass. As expected, these hypo-osmolar IVRs produced statistically significant decreases in IVR masses, showing delivery of liquid to the sheep vagina.

TABLE 2

The in vivo sheep IVR mass change results.

| | Change in IVR Mass | |
|---|---|---|
| IVR Design | Change in mass (mg) | % of change in placebo mass (%) |
| Iso-osmolar IVR | | |
| Acetate Buffer Matrix | −109 ± 15* | −240 ± 32* |
| Hypo-osmolar IVRs | | |
| 97% Water/3% Glycerin Reservoir | −416 ± 55* | −916 ± 121* |
| DDI Water Reservoir | −860 ± 177* | −1892 ± 389* |
| DDI Water Matrix | −404 ± 3* | −888 ± 7* |
| Hyper-osmolar IVRs | | |
| 70% Acetate Buffer/30% Glycerin Matrix | 276 ± 30* | 608 ± 67* |
| 100% Glycerin Reservoir | 955 ± 86* | 2103 ± 189* |
| 70% Glycerin/30% Water Reservoir | 916 ± 85* | 2016 ± 187* |

Data are mean ± SEM (*$p < 0.05$ compared with placebo IVR control data, Student's two-tailed t-test with unequal variance and sample size). The placebo IVRs resulted in an mean change in IVR mass from day 0 to day 5 of 46 ± 2 mg. Negative changes in mass indicate a loss or delivery or release of fluid from the IVR. Positive changes indicate vaginal fluid or water was absorbed into the IVR from the vaginal cavity.

Example 46

IVR Mechanical Testing: Force to Compression Data

The IVR mechanical properties of the IVRs examined in sheep were tested by measuring the amount of force needed to compress the ring one-tenth of its initial outer diameter using a cyclical compression-relaxation program on an Instron 3342 (Norwood, Mass.) with Bluehill Lite (Norwood, Mass.) software. The ring was placed in a small slotted base and held upright by minimal pressure from a probe attached to the upper pressure transducer. The IVRs were compressed 10% of their outer diameter at a rate of 1 mm/sec. The force (N) at that compression was measured. The results of the force testing before and after insertion in sheep can be seen in Table 3. All IVRs exhibited a force at 10% compression range between 0.4 N and 2.6 N.

TABLE 3

The force at 10% (of outer diameter) compression.

| IVR Type | Force at 10% compression before, mean ± SD (N) | Force at 10% compression after, mean ± SD (N) |
|---|---|---|
| Placebo (aliphatic thermoplastic PEU) | 1.03 ± 0.08 | 0.71 ± 0.04 |
| Iso-osmolar Acetate Buffer Matrix | 1.08 ± 0.02 | 1.03 ± 0.03 |

TABLE 3-continued

The force at 10% (of outer diameter) compression.

| IVR Type | Force at 10% compression before, mean ± SD (N) | Force at 10% compression after, mean ± SD (N) |
| --- | --- | --- |
| DDI water matrix | 1.30 ± 0.13 | 1.28 ± 0.09 |
| 70/30 wt % Acetate Buffer/Glycerol | 1.16 ± 0.04 | 1.21 ± 0.07 |
| 100% Glycerol Reservoir | 2.55 ± 0.44 | 1.99 ± 0.44 |
| 70/30 wt % Glycerol/Water Reservoir | 0.44 ± 0.04 | 0.62 ± 0.06 |

Example 47

Measuring Glycerol on Weck-Cel® Swabs

Selected Weck-Cel® swabs (6 hours, 3 days, 5 days) from the sheep studies involving two IVRs containing glycerol (hydrophilic aliphatic thermoplastic polyurethane 70/30 wt % glycerol/DDI water reservoir IVR and the TECOPHILIC HP-60D-35 100 wt % reservoir IVR described previously) were analyzed for glycerol content using the HPLC method of Example 53.1. The swabs were submerged in 20 mL of phosphate buffered saline (PBS, 25 mM and pH 7.4) for 1 week. The amount of glycerol present on each swab can be observed in Table 4. The results show the presence of glycerol, which was released from the devices in the sheep vaginal tract during the 5 day study. The amount of glycerol present on each swab ranged from approximately 40 to 10,000 μg.

TABLE 4

Amount of Glycerol on Weck-Cel ® swabs.

| IVR Type | Time (hrs) | Amount glycerol (μg) |
| --- | --- | --- |
| 70/30 wt % glycerol/water reservoir | 6 | 10705 |
|  | 72 | 49 |
|  | 120 | 129 |
| 100 wt % glycerol reservoir | 6 | 44 |
|  | 72 | 46 |
|  | 120 | 116 |

Example 48

Measuring Glycerol Content in IVRs

The glycerol content of the 70/30 wt % glycerol/water reservoir IVR and 100 wt % glycerol reservoir IVR were measured by extracting the contents of the IVR after the sheep study and the inner fluid was analyzed for glycerol using the HPLC method of Example 53.1. The amount of glycerol was found to be 0.175 wt % and 0.144 wt %, respectively, indicating over 99% glycerol release from the IVRs.

Example 49

In Vitro Release of $H_2O$ or MeOH into $D_2O$ Release Media

The purpose of these studies was to examine the release characteristics of various embodiments into a known volume $D_2O$ and to show the movement of liquid across the device membrane. IVRs (hydrophilic silicone polyurethane matrix (Example 17), TECOPHILIC SP-80A-150 matrix (Example 16.2), TECOPHILIC HP-93A-100 reservoir, and hydrophilic aliphatic thermoplastic polyurethane reservoir (Example 32) with a 1.5 mm wall thickness) were immersed in DDI water for 3 days to fill (27 gauge needles were used to fill the lumen of the reservoir devices prior to immersion) and then placed in 30 mL of $D_2O$. The IVRs were submerged and held in the solution with 7 gram stainless steel washers. All samples were maintained at room temperature without stirring. Samples were obtained at 1, 3, 6, and 24 hours. The release study was stopped after 24 hours, because the samples achieved an equilibrium level of release. The volume collected at each time point was 600 μL. After sample collection, 600 μL of $D_2O$ was added back to the release media to return the volume to 30 mL and the calculation of the amount release was adjusted for this dilution. A 10 μL volume of acetone was added to each sample as an internal standard. The samples were analyzed by measuring the water released from the IVRs into the surrounding release media using proton NMR techniques with a DMX 400 MHz NMR Spectrometer (Bruker Corporation, Billerica, Mass.). $^1$H NMR ($D_2O$, δ/ppm): 2.06 (acetone) and 4.65 (water). The acetone peak was set to a constant value as an internal standard. Using this aqueous testing method, the results show equilibrium release was achieved between 6 and 24 hours. This shows that protons can diffuse across these membranes in an aqueous environment. The results are shown below in Table 5.

TABLE 5

% Cumulative $H_2O$ release into $D_2O$.

| Time (hr) | hydrophilic silicone polyurethane matrix (%) | TECOPHILIC SP-80A-150 matrix (%) | TECOPHILIC HP-60D-100 reservoir (%) | hydrophilic aliphatic thermoplastic polyurethane reservoir, 1.5 mm wall (%) |
| --- | --- | --- | --- | --- |
| 1 | 64 | 67 | 72 | 47 |
| 3 | 72 | 72 | 72 | 60 |
| 6 | 82 | 77 | 73 | 71 |
| 24 | 101 | 73 | 72 | 76 |

It is challenging to measure the release of water using $D_2O$, because of the proton exchange from one oxygen in water to the next. Therefore, we used the lowest molecular weight surrogate for water (methanol) to demonstrate diffusion across the membrane of a low molecular weight molecule. IVRs (hydrophilic silicone polyether urethane matrix (Example 17), TECOPHILIC SP-80A-150 matrix (Example 16.2), hydrophilic aliphatic thermoplastic polyurethane reservoir with a 0.7 mm wall thickness (Example 31), and hydrophilic aliphatic thermoplastic polyurethane reservoir with a 1.5 mm wall thickness (Example 32)) were immersed in a 70/30 v % DDI water/methanol mixture for 24 hours to fill (27 gauge needles were used to fill the lumen of the reservoir devices prior to immersion) and then placed in 30 mL of $D_2O$. The IVRs were submerged and held in the solution with 7 gram stainless steel washers to make sure the devices were completely immersed. All samples were maintained at room temperature without stirring. Samples were obtained at 1, 3, and 6 hours and 1, 2, 3, 4, and 5 days. The volume collected at each time point was 600 μL. After sample collection, 600 μL of $D_2O$ was added back to the release media to bring the volume back to 30 mL and this dilution was compensated for in the release calculation known to those skilled in the art. A 10 μL volume of acetone was added to each NMR sample as an internal standard for integration and determination of the concentration of the released methanol. The samples were analyzed by measuring the methanol released from the IVR into the surrounding release media using proton NMR with a DMX 400 MHz NMR Spectrometer (Bruker Corporation, Billerica, Mass.). $^1$H NMR (D$_2$O, δ/ppm): 2.06 (acetone) and 3.15 (methanol). The acetone peak was set to a constant value as an internal standard. The results show that by changing the wall thickness of the device, release of the low molecular weight model for water can be modulated. The results are shown below in Table 6.

TABLE 6

% Cumulative MeOH release into D$_2$O.

| Time (hr) | hydrophilic silicone polyurethane matrix (%) | TECOPHILIC SP-80A-150 matrix (%) | hydrophilic aliphatic thermoplastic polyurethane reservoir, 0.7 mm wall (%) | hydrophilic aliphatic thermoplastic polyurethane reservoir, 1.5 mm wall (%) |
|---|---|---|---|---|
| 1  | 15 | 63 | 61  | 76  |
| 3  | 16 | 86 | 86  | 101 |
| 6  | 20 | 94 | 105 | 120 |
| 24 | 21 | 92 | 108 | 123 |
| 48 | 21 | 92 | 103 | 121 |
| 72 | 22 | 89 | 103 | 120 |
| 96 | 21 | 87 | 103 | 119 |

Example 50

K-Y® Brand Jelly Lubricant Release Study

The purpose of this study was to examine the in vitro release of the lubricant K-Y® Brand Jelly from IVRs having lumens and pores. Methylene blue was used to quantify the amount of lubricant released. The following IVRs were studied: the dual reservoir IVR (Example 38), TECOFLEX IVR reservoir with pores (Example 37), and TECOFLEX IVR reservoir with pores compressed to an outer diameter of 45.2 mm (Example 37). All IVRs were filled with a 0.22 wt % mixture of methylene blue in K-Y® Brand Jelly as has been described and then placed in 50 mL of DDI water at 37° C. and a stir speed of 80 rpm. Samples were obtained at 6 hours and 1, 2, 3, 4, and 5 days. Sample size was 1.5 mL and 1.5 mL of DDI water was immediately replaced to maintain a constant release media volume. Samples were analyzed in a Synergy 2 (BioTek, Inc., Winooski, Vt.) plate reader for absorbance at a wavelength of 662 nm.

The results of the K-Y® Brand Jelly in vitro release study can be seen in Table 7. The amount of K-Y® Brand Jelly released was found by multiplying the amount in milligrams of released methylene blue by 465, because the initially loaded mixture of K-Y® Brand Jelly was 0.22 wt % methylene blue. The results show the ability to release K-Y® Brand Jelly ranging from approximately 7 to 315 mg daily from a reservoir IVR constructed from a hydrophobic polymer containing pores. To support the claim in this embodiment, the compressed IVR showed a lower daily release possibly due to the closure of some of the pores from compression of the outer diameter while other pores were opened by that compression as per the claim.

TABLE 7

K-Y ® Brand Jelly release at each time point from each type of device.

| Time (hr) | TECOFLEX reservoir IVR (mg) | Compressed TECOFLEX reservoir IVR (mg) | Dual Reservoir IVR (mg) |
|---|---|---|---|
| 6   | 6.7  | 14  | −5.4 |
| 24  | 123  | 103 | 61   |
| 48  | 174  | 117 | 76   |
| 72  | 315  | 141 | 49   |
| 96  | 114  | 167 | 27   |
| 120 | −2.7 | 37  | 30   |

Example 51

IVR Mechanical Testing: Force to Compression Data

The IVR mechanical properties of the IVRs used in the release study above were tested by measuring the amount of force needed to compress the ring one-tenth of its initial diameter using a cyclical compression-relaxation program on an Instron 3342 (Norwood, Mass.) with Bluehill Lite (Norwood, Mass.) software. The ring was placed in a small slotted base and held upright by minimal pressure from a probe attached to the upper pressure transducer. The IVRs were compressed 10% of their outer diameter at a rate of 1 mm/sec. The force (N) at that compression was measured. The results of the force testing before and after the release study can be seen in Table 8. All IVRs exhibited a force at 10% compression range between 0.6 N and 1.1 N.

TABLE 8

The force to compress the IVR 10% of outer diameter.

| IVR Type | Force at 10% compression before release study (N) | Force at 10% compression after release study (N) |
|---|---|---|
| TECOFLEX reservoir IVR | 0.97 | 0.84 |
| Compressed TECOFLEX reservoir IVR | 1.06 | 0.66 |
| Dual Reservoir IVR | 0.72 | 0.80 |

Example 52

Pod Release Studies

1. *Lactobacillus* Release Studies

The purpose of these studies was to examine the in vitro release of *Lactobacillus* in various embodiments, including pellets inside pods (Example 20), pellets without pods (Example 21), and pellets containing HPC/*Lactobacillus* (Example 22). *Lactobacillus* is a probiotic agent and in this embodiment it would be useful to deliver a probiotic agent intravaginally. A matrix pod holder and a reservoir pod holder described previously (Examples 18 and 19 above) were fitted with a pod containing a 100% *Lactobacillus* pellet (0.17 g) described above in Example 20. The IVRs were placed in 25 mL of DDI water at 37° C. and a stir speed of 80 rpm. Samples were taken at 6 hours and 1, 2, 3, 4, and 5 days. Sample size obtained was 5 mL and 5 mL of DDI water was immediately replaced to keep the release media volume constant. Samples were analyzed for *Lactobacillus* release in a cuvette for UV absorbance at a wavelength of 220 nm.

In another embodiment, the study above was repeated but with pellets made from 50/50 wt % HPC/*Lactobacillus* as described above in Example 22 to examine the effect of HPC on release rate. A 10 mL volume of DDI water was used as release media and the sample size obtained was 4 mL. Samples were analyzed for *Lactobacillus* release using UV absorbance at a wavelength of 220 nm.

A matrix pod holder was fitted with a 100% *Lactobacillus* pellet (Example 21), without the pod covering to examine the effect on release rate. The pellet was attached into the pod holder using the TECOFLEX 1-MP adhesive glue to cover one side of the pellet. After curing the glue overnight, the IVR was placed in 25 mL of DDI water at 37° C., with a stir speed of 80 rpm. Samples were obtained at 6 hours and 1, 2, 3, 4, and 5 days. The sample size was 5 mL and 5 mL of DDI water was immediately replaced. Samples were analyzed for *Lactobacillus* release in a cuvette for UV absorbance at a wavelength of 220 nm.

The results for all of the *Lactobacillus* in vitro release studies are shown below in Table 9. These results show the ability to release/deliver *Lactobacillus* from a variety of different pellet/pod combinations with daily release rates ranging between approximately 0 to 68 mg daily.

TABLE 9

*Lactobacillus* release at each time point from each type of device.

| Time (hr) | pellet, no pod, matrix IVR (mg) | *Lactobacillus* only, pod, reservoir IVR (mg) | *Lactobacillus* only, pod, matrix IVR (mg) | 50/50 wt % HPC/*Lactobacillus* pellet, pod, matrix IVR (mg) | 50/50 wt % HPC/*Lactobacillus* pellet, pod, reservoir IVR (mg) |
|---|---|---|---|---|---|
| 6 | 0.0 | 4.2 | 1.4 | NA | NA |
| 24 | 68 | 2.2 | 1.0 | 2.6 | 4.0 |
| 48 | 17 | 1.3 | 2.4 | 3.9 | 11 |
| 72 | 13 | 4.2 | 8.9 | 2.5 | 1.4 |
| 96 | 3.5 | 15 | 12 | 2.6 | 2.9 |
| 120 | 3.2 | 17 | 15 | −0.5 | 0.8 |

2. IVR Mechanical Testing: Force to Compression Data

The IVR mechanical properties of the IVRs from the *Lactobacillus* release study above were tested by measuring the amount of force needed to compress the ring one-tenth of its initial diameter using a cyclical compression-relaxation program on an Instron 3342 with Bluegill Lite software. The ring was placed in a small slotted base and held upright by minimal pressure from a probe attached to the upper pressure transducer. The IVRs were compressed 10% of their outer diameter at a rate of 1 mm/sec. The force (N) at that compression was measured. The results of the force testing before and after the release study can be seen in Table 10. All IVRs exhibited a force at 10% compression range between 0.2 N and 1.3 N.

TABLE 10

The force at 10% of outer diameter compression.

| IVR Type | Force at 10% compression before release study (N) | Force at 10% compression after release study (N) |
|---|---|---|
| *Lactobacillus* pod matrix IVR | 1.15 | 1.26 |
| *Lactobacillus* pod reservoir IVR | 0.64 | 0.20 |

3. HEC Release Study

The purpose of the following studies was to examine the release of HEC in a pod/pellet combination. Rhodamine B Isothiocyanate-Dextran was used to quantify the HEC release. A matrix pod holder and a reservoir pod holder described in Examples 18 and 19 above were fitted with a pod containing a 99/1 wt % HEC/Rhodamine B Isothiocyanate-Dextran pellet (Example 23). The IVRs were placed in 3 mL of DDI water at 37° C. and a stir speed of 80 rpm. Samples were taken at days 1, 2, 3, 4, and 5. Sample size was 1.5 mL and 1.5 mL of DDI water was added back. Samples were analyzed in a PerkinElmer LS 55 luminescence spectrometer (PerkinElmer, Inc., Waltham, Mass.) (excitation and emission wavelengths were 570±5 nm and 590±5 nm respectively). In one embodiment, one of the pods had a clear piece of adhesive tape placed over the orifice to simulate a possible solution to keep the contents from leaking during storage. This tape was removed prior to the release study.

The HEC release at each time point can be seen in Table 11. The results show the ability to release HEC from a pod in daily amounts up to 1.65 mg.

TABLE 11

HEC release from each device.

| Time (hr) | Pod matrix IVR (mg) | Pod reservoir IVR (mg) |
|---|---|---|
| 24 | 0.24 | 0.42 |
| 48 | 0.48 | 0.78 |
| 72 | 0.53 | −0.19 |
| 96 | −0.21 | 0.38 |
| 120 | 0.85 | 1.65 |

4. IVR Mechanical Testing: Force to Compression Data

The mechanical properties of the IVRs from Examples above were tested by measuring the amount of force needed to compress the ring one-tenth of its initial diameter using a cyclical compression-relaxation program on an Instron 3342 with Bluehill Lite software. The ring was placed in a small slotted base and held upright by minimal pressure from a probe attached to the upper pressure transducer. The IVRs were compressed 10% of their outer diameter at a rate of 1 mm/sec. The force (N) at that compression was measured. The results of the force testing before and after the release study can be seen in Table 12. All IVRs exhibited a force at 10% compression range between 0.37 N and 1.48 N.

TABLE 12

The force on the IVR at 10% of outer diameter compression.

| IVR Type | Force at 10% compression before (N) | Force at 10% compression after (N) |
|---|---|---|
| HEC pod, matrix IVR | 1.27 | 1.48 |
| HEC pod, reservoir IVR | 0.80 | 0.37 |

Example 53

Glycerol Release Studies

1. Glycerol Quantification by HPLC

Glycerol was quantified by the method of D. Stadnik, L. Gurba, S. Blazej, B. Tejchman-Malecka, Quantitative Analysis of Glycerol in Aqueous Pharmaceutical Preparations by RP-HPLC. 60th *Annual Pittsburgh Conference on Analytical Chemistry and Applied Spectroscopy* (poster presentation), Pittsburgh, Pa. USA (2009). This method uses the oxidation of glycerol to formaldehyde with periodate and the subsequent reaction of the formaldehyde with acetylacetone in the presence of ammonium acetate to form 3,5-diacetyl-1,4-dihydrolutidine (DADHL), which is the final product detected by HPLC. To determine the amount of glycerol released from each sample, the samples were diluted from 1:10 to 1:500 depending on the sample type or time point. A volume of 100 µL from each diluted sample was transferred to an HPLC vial, and 200 µL of 3 mM sodium periodate solution in acetate buffer containing 1 M ammonium acetate and 0.6 M acetic acid and 500 µL of acetylacetone (1% v/v in IPA, prepared fresh) was added to this vial. The vial was placed at 50° C. in a bench top shaker for 20 min and then analyzed via the following gradient HPLC method to determine the glycerol concentration in release media samples by utilizing the above reaction. Reacted samples were injected onto a Zorbax ODS C18, 4.6 mm×250 mm (5 µm pore size) column (Agilent Technologies, Inc., Santa Clara, Calif.), and a gradient method was run (Table 13). The final product DADHL was detected at $\lambda$=410 nm, with an average retention time of 3.7 min. Solutions of glycerol in DDI water with known concentrations (ranging from 0.261 to 66.9 µg/mL) were reacted and injected onto the column at the beginning of each HPLC sequence to create a linear calibration curve relating peak area to the concentration (mg/mL) of the original glycerol solution with peak areas ranging from 6.7 to 322.3. The calibration curve was fitted using linear regression ($R^2$=0.997). A peak was determined to represent DADHL elution from the column if the retention time from sample injections matched that of standard injections in the same sequence. An Agilent 1200 HPLC with diode array detector (Agilent Technologies, Inc., Santa Clara, Calif.) was used.

TABLE 13

A 10-minute HPLC method used for DADHL quantification.

| Time (min) | Flow (mL/min) | % Solvent A | % Solvent B |
|---|---|---|---|
| 0 | 1 | 60 | 40 |
| 6 | 1 | 65 | 35 |
| 8 | 1 | 70 | 30 |
| 9 | 1 | 60 | 40 |
| 10 | 1 | 60 | 40 |

Solvent A was 0.1 v % TFA in water and Solvent B was 0.1 v % TFA in 90/10 v % acetonitrile/water.

2. Glycerol Release Study

The purpose of the following studies was to examine the in vitro glycerol release from various IVDs of the present technology. The glycerol release from the following types of IVDs was measured: hydrophilic aliphatic thermoplastic polyurethane (cross-section 5.5 mm×wall thicknesses of 0.7 mm or 1.5 mm (Examples 29 or 30)), multi-lumen device (Example 36), tampon-shaped device (Example 40), K-Y® Brand LIQUIBEADS® in pod holder (Example 24). All devices have been described above and were filled with glycerol with the exception of the K-Y® Brand LIQUIBEADS® pod holder device. All devices were placed in 400 mL of DDI water at 37° C., with a stir speed of 80 rpm. Samples were obtained at 6 hours and 1, 2, 3, 4, and 5 days (only K-Y® Brand LIQUIBEADS® device sampling was stopped after 24 hours due to complete dissolution of the K-Y® Brand LIQUIBEADS® insert). Sample size was 1 mL and water was not replaced after each collection. The internal lumens of the IVRs (excluding the K-Y® Brand LIQUIBEADS® device) also were analyzed for glycerol content after day 5.

The results for all glycerol in vitro release studies can be seen in Table 14. Note the release for the K-Y® Brand LIQUIBEADS® device is in milligrams and not percent loaded glycerol. The results show the ability to delivery/release glycerol from a variety of devices.

TABLE 14

Cumulative glycerol release from each type of device.

| Time (hr) | Multi-Lumen device (%) | Tampon-shaped device (%) | 0.7 mm wall thickness device (%) | 1.5 mm wall thickness device (%) | K-Y® Brand LIQUIBEADS device (mg) |
|---|---|---|---|---|---|
| 6 | 103 | 8.2 | 3 | 7 | 272 |
| 24 | 109 | 51 | 76 | 41 | 263 |
| 48 | 111 | 83 | 104 | 123 | NA |
| 72 | 107 | 84 | 108 | 123 | NA |
| 96 | 102 | 69 | 110 | 128 | NA |
| 120 | 106 | 95 | 111 | 132 | NA |

The multi-lumen,-tampon-shaped, 0.7 mm wall thickness, and 1.5 mm wall thickness devices were loaded with approximately 0.51, 2.7, 2.2, and 0.82 g of glycerol, respectively.

3. IVR Mechanical Testing: Force to Compression Data

The mechanical properties of select IVDs in the glycerol release study from above were tested by measuring the amount of force needed to compress the ring one-tenth of its initial diameter using a cyclical compression-relaxation program on an Instron 3342 with Bluehill Lite software. The ring was placed in a small slotted base and held upright by minimal pressure from a probe attached to the upper pressure transducer. The IVRs were compressed 10% of their outer diameter at a rate of 1 mm/sec. The force (N) at that compression was measured. The results of the force testing before and after the release study can be seen in Table 15. All IVDs exhibited a force at 10% compression ranging between 0.68 N to 1.06 N.

TABLE 15

The force at 10% of outer diameter compression.

| IVR Type | Force at 10% compression before (N) | Force at 10% compression after (N) |
|---|---|---|
| 0.7 mm wall | 0.68 | 0.70 |
| 1.5 mm wall | 1.06 | 0.92 |
| multi-lumen IVR | 0.81 | 0.84 |

Example 54

Evaporation Study, Temperature Change

The present study demonstrates the controlled in vitro loss/delivery of water or water vapor from the IVDs listed below. A TECOPHILIC SP-80A-150 IVR (Example 16.2) was immersed in 100 mL DDI water for 3 days to hydrate the polymer. A temperature probe was adhered to the surface of the hydrated IVR and to the surface of an identical dry, control IVR. A separate temperature probe also was used to monitor the room temperature. The IVRs were placed at room temperature on the bench-top and temperature was recorded at 5, 10, 15, and 30 minutes and 1, 3, and 28 hours.

The results of this in vitro study can be seen in Table 16. When the surface of the IVR is in contact with air, the surface cooled by 5.5° C. This surface cooling indicates the enthalpically driven change in state from condensed, liquid water to gaseous water, known as evaporation. This shows the delivery of water vapor from the IVR surface.

TABLE 16

Evaporation temperatures monitored.

| Time (min) | Wet IVR (active) (° C.) | Dry IVR (control) (° C.) | Air/ Room (° C.) |
|---|---|---|---|
| 0 | 19.5 | 22.6 | 21.9 |
| 5 | 17.3 | 22.4 | 21.9 |
| 10 | 17.0 | 22.4 | 22.0 |
| 15 | 16.6 | 22.0 | 22.1 |
| 30 | 16.4 | 21.9 | 21.9 |
| 60 | 17.0 | 21.9 | 22.3 |
| 180 | 19.4 | 22.1 | 22.1 |
| 1680 | 23.6 | 23.3 | 24.0 |

Example 55

Evaporation Study, Mass Change

In this embodiment, an evaporation study was performed to determine the fluid release rate in a partially enclosed container to provide an in vitro model of the vaginal space and demonstrate the controlled release of water or water vapor. A TECOPHILIC SP-80A-150 IVR (dry weight 2.88 g, hydrated weight 5.84 g, 2.97 g water) (Example 16.2), a TECOPHILIC HP-93A-100 reservoir IVR (dry weight 0.93 g, hydrated weight 3.70 g, 2.77 g water) (Example 35) and a hydrophilic silicone polyurethane matrix (dry weight 2.65 g, hydrated weight 3.27 g, 0.62 g water) (Example 17) were immersed (27 gauge needles were used to fill the inner lumen of the reservoir device prior to immersion) in 100 mL of DDI water for 3 days to hydrate the polymer. The IVRs were then placed in a 400 mL glass jar with a ¼ inch hole in the top of the jar. The jars were kept at room temperature and the change in mass was monitored at various time points over 10 days (121.5 hours for the hydrophilic silicone polyurethane matrix device).

TABLE 17

Evaporation mass change study.

| Time (hrs) | DDI Water TECOPHILIC SP-80A-150 Matrix IVR Mass Loss (%) | DDI Water TECOPHILIC HP-60D-100 Reservoir IVR Mass Loss (%) | Hydrophilic silicone polyurethane matrix IVR Mass Loss (%) |
|---|---|---|---|
| 0.5 | 0.3 | 0.3 | 1.5 |
| 1.5 | 0.8 | 0.9 | 5.0 |
| 3 | 1.6 | 1.7 | 9.3 |
| 6 | 3.0 | 3.3 | 20 |
| 25.5 | 13.6 | 14.1 | 47 |
| 50 | 26.5 | 27.9 | 75 |
| 72 | 37.5 | 40.0 | 86 |
| 96 | 50.6 | 54.5 | 96 |
| 121.5 | 63.6 | 68.7 | 101 |
| 137 | 75.7 | 81.2 | NA |
| 168 | 85.7 | 87.5 | NA |
| 240 | 98.3 | 91.3 | NA |
| Average Rate of mass loss (µL/hr): | 12.2 | 11.3 | 5.0 |

The results of the in vitro study can be seen in Table 17. By day 10, both TECOPHILIC devices had delivered over 90% of their water at a rate of 12 µL/hr and by 121.5 hours, the hydrophilic silicone polyurethane matrix device had delivered just over 100% of its water at a rate of 5.0 µL/hr. The results show an extended delivery of water over several days.

Example 56

IVR Mechanical Testing: Force to Compression Data

The IVR mechanical properties of the TECOPHILIC SP-80A-150 IVR and hydrophilic silicone polyurethane IVR from the evaporation study above were tested by measuring the amount of force needed to compress the ring one-tenth of its initial diameter using a cyclical compression-relaxation program on an Instron 3342 with Bluehill Lite software. The ring was placed in a small slotted base and held upright by minimal pressure from a probe attached to the upper pressure transducer. The IVR was compressed 10% of its outer diameter at a rate of 1 mm/sec. The force (N) at that compression was measured. The TECOPHILIC SP-80A-150 IVR exhibited a force at 10% compression ranging from 1.37 N before the study to 1.12 N at the completion of the study and the hydrophilic silicone polyurethane matrix IVR exhibited a force at 10% compression ranging from 0.48 N before the study to 0.50 N at the completion of the study.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group or combinations thereof.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges, which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An intravaginal device comprising:
   a first segment comprising:
      an outer surface and
      a lumen containing an aqueous lubricant,
   wherein the first segment comprises a water-swellable, hydrophilic polyether polyurethane and is configured to deliver the contents of the lumen to the outer surface by diffusion.

2. The intravaginal device of claim 1 wherein the aqueous lubricant has a pH of about 3 to about 6.

3. The intravaginal device of claim 1 wherein the aqueous lubricant comprises one or more salts, nonaqueous solvents, C1-8 carboxylic acids, glucose, antioxidants, preservatives, surfactants, fragrance, flavoring agents, colors, or sweeteners.

4. The intravaginal device of claim 3 where the aqueous lubricant has a pH from 3 to 6.

5. The intravaginal device of claim 1 wherein the aqueous lubricant comprises one or more salts, propylene glycol, glycerol, lactic acid, acetic acid, glucose, BHT, ascorbic acid, sorbital, sorbic acid, parabens, EDTA, sodium benzoate, tocopherol, polysorbate 20, polysorbate 60, sorbate salts, saccharine, or aspartamate.

6. The intravaginal device of claim 1 wherein the aqueous lubricant is buffered at an acidic pH to promote the natural acidity of the vagina.

7. The intravaginal device of claim 1 wherein the aqueous lubricant comprises vaginal fluid simulant, about 5 to about 50 mM lactic acid, an acetic acid buffer at a pH of about 3.5 to about 5.0, and optionally about 5 to about 50 mM glucose.

8. The intravaginal device of claim 1 wherein the aqueous lubricant comprises from 4 wt % to 90 wt % glycerol.

9. The intravaginal device of claim 1 wherein the aqueous lubricant comprises from 60 wt % to 95 wt % glycerol.

10. The intravaginal device of claim 1 further comprising an agent selected from the group consisting of drugs and probiotics.

11. The intravaginal device of claim 10 wherein the agent is a probiotic selected from the group consisting of *Lactobacillus*, vitamins, and minerals.

12. The intravaginal device of claim 1 further comprising one or more additional segments, each of which comprises a polymer, an outer surface and optionally a lumen.

13. The intravaginal device of claim 12 wherein the polymer of the one or more additional segments is a hydrophobic elastomer.

14. The intravaginal device of claim 12 wherein the hydrophobic elastomer is silicone, silicone polyurethane, polyurethane, or ethylene-vinyl acetate copolymer.

15. The intravaginal device of claim 1 wherein the device is refillable with aqueous lubricant.

16. The intravaginal device of claim 1 wherein the device is a intravaginal ring.

17. The intravaginal device of claim 16 further comprising a spring configured to support the ring or any part thereof.

18. The intravaginal device of claim 16 wherein the spring is embedded in the ring and encircles at least one lumen of the ring.

19. A method of lubrication comprising administering an intravaginal device of claim 1 to a female in need of vaginal lubrication.

20. The method of claim 19 wherein the device delivers 0.001-1000 mg of aqueous lubricant to the outer surface of the device per day.

21. The method of claim 19 wherein the lubricant is delivered over a period of time ranging from 1 hour to 1 month.

22. The method of claim 19 wherein the intravaginal device is administered to the female to relieve vaginal dryness from vaginitis, inflammation of the vagina due to the thinning and shrinking of the tissues, decreased lubrication, sexual arousal disorder, menopause, drug-induced vaginal dryness, dyspareunia, sexual pain disorder, menopause, pregnancy, hormone imbalance, anxiety and diabetes, or other related disorders.

23. The method of claim 19 wherein the aqueous lubricant is water, hypo-osmolar solution, iso-osmotic solution, hyperosmotic solution, or gel.

24. The method of claim 19 wherein the aqueous lubricant comprises one or more salts, nonaqueous solvents, C1-8 carboxylic acids, glucose, antioxidants, preservatives, surfactants, fragrance, flavoring agents, colors, or sweeteners.

25. The method of claim 19 wherein the aqueous lubricant comprises from 4 wt % to 90 wt % glycerol.

26. The intravaginal device of claim 1 wherein the first segment is configured to deliver 0.1-1000 mg of aqueous lubricant to the outer surface of the device per day.

27. The intravaginal device of claim 1 wherein the first segment is configured to deliver 1-1000 mg of aqueous lubricant to the outer surface of the device per day.

28. The method of claim 20 wherein the device delivers 0.1-1000 mg of aqueous lubricant to the outer surface of the device per day.

29. The method of claim 20 wherein the device delivers 1-1000 mg of aqueous lubricant to the outer surface of the device per day.

* * * * *